US007687542B2

(12) United States Patent
Reiner et al.

(10) Patent No.: US 7,687,542 B2
(45) Date of Patent: *Mar. 30, 2010

(54) RAPIDLY BIOAVAILABLE TABLET AND CAPSULE FORMULATIONS OF DICLOFENAC

(75) Inventors: Giorgio Reiner, Como (IT); Alberto Reiner, Como (IT)

(73) Assignee: Kowa Pharmaeuticals America, Inc., Montgomery, AL (US)

( * ) Notice: Subject to any disclaimer, the term of this patent is extended or adjusted under 35 U.S.C. 154(b) by 145 days.

This patent is subject to a terminal disclaimer.

(21) Appl. No.: 11/351,611

(22) Filed: Feb. 10, 2006

(65) Prior Publication Data

US 2006/0188565 A1    Aug. 24, 2006

(51) Int. Cl.
*A61K 31/185* (2006.01)
*A61K 31/19* (2006.01)
(52) U.S. Cl. .................. 514/553; 514/557; 514/576
(58) Field of Classification Search ............. 514/553, 514/557, 576; 560/47
See application file for complete search history.

(56) References Cited

U.S. PATENT DOCUMENTS

| | | | |
|---|---|---|---|
| 3,558,690 | A | 1/1971 | Sallmann et al. |
| 4,689,218 | A | 8/1987 | Gazzaniga et al. |
| 5,458,879 | A * | 10/1995 | Singh et al. ........... 424/400 |
| 6,974,595 | B1 | 12/2005 | Reiner et al. |
| 2005/0147671 | A1 | 7/2005 | Reiner et al. |
| 2005/0214363 | A1 | 9/2005 | Reiner et al. |
| 2005/0215643 | A1 | 9/2005 | Reiner et al. |
| 2006/0013896 | A1 | 1/2006 | Reiner et al. |

FOREIGN PATENT DOCUMENTS

| | | |
|---|---|---|
| CA | 2131515 | 9/1994 |
| EP | 0 418 043 B1 | 12/1990 |
| EP | 0 466 640 A2 | 1/1992 |
| GB | A-2 401 547 | 11/2004 |
| WO | WO 94/03160 A | 2/1994 |
| WO | WO 96/14839 A | 5/1996 |
| WO | 97/44023 | 5/1997 |

OTHER PUBLICATIONS

[R] Gennaro et al. (eds.), Remington's Pharmaceutical Science, 18th Edition, Mack Publishing Co., Easton, PA, 1990, only pp. 1110, 1111, 1637, 1846 and 1847 supplied.*
U.S. Appl. No. 11/132,023, filed May 18, 2005, Reiner, et al.
U.S. Appl. No. 11/132,024, filed May 18, 2005, Reiner, et al.
U.S. Appl. No. 11/180,996, filed Jul. 13, 2005, Reiner, et al.
U.S. Appl. No. 11/030,537, filed Jan. 5, 2005, Reiner, et al.
U.S. Appl. No. 11/348,634, filed Feb. 7, 2006, Schellenger et al.
U.S. Appl. No. 11/455,120, filed Jun. 16, 2006, Reiner, et al.
U.S. Appl. No. 11/349,008, filed Feb. 7, 2006, Reiner, et al.

Henry, D., et al; "Variability in risk of gastrointestinal complications with individual non-steroidal anti-inflammatory drugs; results of a collaborative meta-analysis"; BMJ; vol. 312, pp. 1563-1566, (1996).
Walker A.M.; "Quantitative studies of the risk of serious hepatic injury in persons using nonsteroidal antiinflammatory dugs"; Arthritis and Rheumatism. vol. 40, No. 2, pp. 201-108 (1997).
Gutthann, S.P., et al; "Nonsteroidal anti-inflammatory drugs and the risk of hospitalization for acute renal failure"; Arch. Intern. Med., vol. 156, pp. 2433-2439, (1996).
Amidon, G.L., et al; "A theoretical basis for a biopharmaceutic drug classification: The correlation of in vitro drug product dissolution and in vivi bioavailability"; Pharm. Research, vol. 12, No. 3, pp. 413-420, (1995).
Neuvonen, P.J., "The effect of magnesium hydroxide on the oral absorption of ibuprofen, ketoprofen and diclofenac"; Br. J. Clin. Pharmac. vol. 31, pp. 263-266, (1991).
Neuvonen, P.J., et al; "Enhancement of drug absorption by antacids"; Clin. Pharmacokinet. 27 (2): pp. 120-128, (1994).
Neuvonen, P.J., et al; "Effect of magnesium hydroxide on the absorption of tolfenamic and mefenamic acids"; Eur. J. Clin. Pharmacol, 35: pp. 495-501, (1988).
Derendorf, H., et al; "Pharmacokinetics of diclofenac sodium after intramuscular administration in combination with triamcinolone acetate"; Eur. J. Clin. Pharmacol.., 31:363-365 (1986).
Terhaag, B., et al; "Bioavailability of a new effervescent tablet of diclofenac"; Int. J. Clin. Pharmacol. Ther., 38:546-551 (2000).
Lotsch, J. et al; "Popluation pharmacokinetics of fast release oral diclofenac in healthy volunteers: relation to pharmacodynamics in an experimental pain model"; Phamaceutical Research, vol. 17, No. 1, pp. 77-84, (2000).
Marzo, A., et al; "Pharmacokinetics of Diclofenac after oral administration of its potassium salt in sachet an tabled formulations"; Arzneim. Forsch., 50:43-47 (2000).
Reiner, V., et al; "Increased absorption rate of diclofenac from fast acting formulations containing its potassium salt"; Arzneim. Forsch., 51-885-890 (2001).
Fourtillan, J.B. et al; "Etude pharmacocinetique du piroxicam chez l'homme sain"; Therapie, vol. 38, pp. 163-170, (1983).
Brogden, R.N., et al; "Diclofenac sodium: A review of its pharmacological properties and therapeutic use in rheumatic diseases and pain of varying orgin"; Drugs, 20: pp. 24-48, (1980).
Macia, M.A., et al: "Comparative bioavailability of a dispersible formulation of diclofenac and finding of double plasma peaks"; Int. J. Clin Pharmacol. Ther., 33:333-339 (1995).
Bettini, R., et al; "Swelling force development as a result of hydrate formation in diclofenac sodium or nitrofurantoin tablets", S.T.P. Pharma Sciences 10 (4) pp. 335-339, (2000).

(Continued)

Primary Examiner—Lawrence E Crane
(74) Attorney, Agent, or Firm—Clark G. Sullivan; Arnall Golden Gregory LLP

(57) ABSTRACT

The present invention relates to excipients for the production of rapidly bioavailable solid oral dosage forms of diclofenac. In particular, the invention relates to the use of excipients that promote the bioavailability of such formulations, including alkaline buffering agents, gas forming excipients, hygroscopic excipients, water soluble diluents, wetting agents, and particular pharmaceutically acceptable salts.

59 Claims, 6 Drawing Sheets

OTHER PUBLICATIONS

Henrikson, P.A., et al; Absorption and effect of diclofenac sodium after surgical removal of a lower wisdom tooth; Curr. Ther. Res., 31:30-36 (1982).

Degen, P.H., et al; "Pharmacokinetics of diclofenac and five metabolites after single doses in healthy volunteers and after repeated doses in patients"; Xenobiotica, 18:1449-1455 (1988).

Maggi, C.A., et al; "Comparative bioavailability of diclofenac hydroxyethylpyrrolidine vs diclofenac sodium in man"; Eur. J. Clin. Pharmacol., 38:207-208 (1990).

Mendes, G.B.B., et al; "Comparative bioavailability of two suspension formulations of potassium diclofenac in healthy male volunteers"; Int. J. Clin. Pharmacol. Thr., 32:131-135 (1994).

Crook, P.R., et al; "The pharmacokinetics of diclofenac sodium in patients with active rheumatoid disease"; Eur. J. Clin. Pharmacol., 21:331-334 (1982).

Willis. J.V., et al; "The pharmacokinetics of diclofenac sodium following intravenous and oral administration"; Eur. J. Clin. Pharmacol., 16:405-410 (1979).

Willis, J.V., et al; "The influence of food on the absorption of diclofenac after single and multiple oral doses"; Eur. J. Clin. Pharmacol., 19:33-37 (1981).

Reiss, W., et al; "Pharmacokinetics and metabolism of the anti-inflammatory agent Voltaren" Scand. J. Reumatol., Suppl. 22:17-29 (1978).

Physicians' Desk Reference; Novartis Pharmaceutical Corp., pp. 1830-1832 (2000).

Bakshi, R., et al; A double-blind, Placebo-controlled trial comparing the analgesic efficacy of two formulations of Diclofenac in postoperative dental pain; Current Therapeutic Research vol. 52, No. 3, pp. 435-442 Sep. (1992).

Dahlöf, C., et al; Diclofenac-K (50 and 100 mg) and placebo in the acute treatment of migraine; Cephalalagia 13, pp. 20-26 (1993).

McNeely, W., et al; Diclofenac-Potassium in Migraine: A Review; Drugs; 57; pp. 991-1003 (1999).

Mehlisch, D.R., et al; Single-dose therapy with Diclofenac potassium, aspirin, or placebo following dental impaction surgery, Today's Therapeutic Trends 12; (Suppl. 1) pp. 15-31 (1995).

The Diclofenac-K/Sumatriptan Migrain Study Group; Acute treatment of migraine attacks: efficacy and safety of a nonsteroidal anti-inflammatory drug, diclofenac-potassium, in comparison to oral sumatriptan and placebo; Cephalalgia 19, pp. 232-240 (1999).

Ridgway, D.; Analgesics for Acute Pain, Meeting the United States Food and Drug Administration's Requirements for Proof of Efficacy, Clin J. Pain vol. 20, No. 3, May/Jun. pp. 123-132 (2004).

Diener, H-C, et al; Efficacy and tolerability of Diclofenac potassium sachets in migraine: a randomized, double-blind, cross-over study in comparison with Diclofenac potassium tablets and placebo; Blackwell Publishing Ltd. *Cephalalgia* 26, pp. 537-547 (2005).

Hofele, C.M.,. et al; Efficacy and tolerability of diclofenac potassium sachets in acute postoperative dental pain: a placebo-controlled, randomised, comparative study vs. diclofenac potassium tablets; 2006 Blackwell Publishing Ltd. Int. J. Clin Pract, Mar. 2006, 60, 3, pp. 300-307.

Craig, C.R.; Opioid and Nonopioid Analgesics, Modern Pharmacology $4^{th}$ Edition, p. 437 (19+94).

Adkin, D. A., et al; The effect of different concentrations of Mannitol in solution on small intestinal transit: Implications for drug absorption; Pharmaceutical Research, vol. 12, No. 3 (1995).

Adkin, D.A., et al; The effect of Mannitol on the oral bioavailability of Cimetidine; Journal of Pharmaceutical Sciences vol. 84, No. 12, Dec. (1995).

Kumar, A., et al.; The Mystery Ingredients: Sweeteners, Flavorings, Dyes and Preservatives in Analgesic/Antipyretic, Antihistamine/Decongestant, Cough and Cold, Antidiarrheal, and Liquid Theophylline Preparations; Pediatrics vol. 91 No. 5 May (1993).

Massiou. H., et al.; Effectiveness of oral Diclofenac in the acute treatment of common migraine attacks: a double-blind study versus placebo; Cephalalgia 11 (1991).

Del Bene, E., et al; Intramuscular Treatment of Migraine Attacks Using Diclofenac Sodium: A Crossover Clinical Trial; The Journal of International Medical Research; 15: 44-48 (1987).

McNeely W et al: "Diclofenac-potassium in migraine: a review." DRUGS Jun. 1999, vol. 57, No. 6, Jun. 1999, pp. 991-1003, XP009077504.

Database Internet [Online] Feb. 2005, NOVARTIS PHARMA: "Voltaren Dispers" XP002434112 retrieved from INTERNET accession No. http://www.fachinfo.de/pdf/00/59/005941.pdf.

* cited by examiner

MEAN PLASMA CONCENTRATION-TIME PROFILE OF DICLOFENAC MEASURED IN ALL VOLUNTEERS AFTER ORAL ADMINISTRATION OF R (VOLTARENE® RAPIDE) FORMULATION. LINEAR SCALE. VERTICAL BARS ARE SD.

US 7,687,542 B2

RAPIDLY BIOAVAILABLE TABLET AND CAPSULE FORMULATIONS OF DICLOFENAC

RELATIONSHIP TO PRIOR APPLICATIONS

The present application claims priority to U.S. Ser. No. 11/180,996, filed Jul. 13, 2005 (pending), and U.S. Ser. No. 11/030,537, filed Jan. 5, 2005 (pending). In turn, the foregoing applications claim priority to U.S. Ser. No. 09/524,747, filed Mar. 14, 2000 (granted as U.S. Pat. No. 6,974,595), which claims priority to U.S. Ser. No. 09/192,493, filed Nov. 17, 1998 (abandoned), which claims priority to PCT/EP97/02709, filed May 15, 1997, which claims priority to Italian App. No. MI96A000992, filed May 17, 1996. The contents of the foregoing applications are incorporated by reference as if fully set forth herein.

FIELD OF THE INVENTION

The present invention relates to excipients for the production of rapidly bioavailable solid oral dosage forms of diclofenac. In particular, the invention relates to the use of excipients that promote the bioavailability of such formulations, including alkaline buffering agents, gas forming excipients, hygroscopic excipients, water soluble diluents, wetting agents, and particular pharmaceutically acceptable salts.

BACKGROUND OF THE INVENTION

Pharmaceutical excipients play a crucial role in the development of solid oral dosage forms. Excipients influence the processability of the powders and granulates used to form solid oral dosage forms, and are selected to assure uniform weights and drug content among unit doses within and among batches. Excipients also influence numerous physical properties of a drug dosage form, including hardness, friability, and ease of disintegration/dissolution. Excipients also influence the bioavailability of a drug when orally ingested by impacting the rate at which the product dissolves in the gastrointestinal tract, the solubility of the drug in the gastrointestinal tract, and the portion of the GI tract in which the drug is released.

When rapid bioavailability is desired, preferred modes of administration include parenteral, inhalation, mucosal and buccal administration. Tablets and capsules are generally available only in immediate release, extended release, and delayed release formats, and are not typically employed when rapid bioavailability is desired because of the time it takes for the dosage form to dissolve, and the resulting delay in gastrointestinal absorption. The present inventors recently proposed in PCT/EP97/02709 (published as WO 97/44023) a novel delivery system for orally delivering diclofenac that employed an alkali metal bicarbonate to accelerate the bioavailability of diclofenac from numerous oral dosage forms, including tablets, powders for dissolution in water, gum, chewable tablets, and liquids, among others. The current application claims priority to WO 97/44023 and incorporates the application's contents by reference.

Currently marketed forms of diclofenac tablets contain various pharmaceutical excipients. For example, diclofenac sodium 25 mg film-coated tablets marketed by Novartis Healthcare as Novapirina® contain colloidal silica, cellulose, lactose, magnesium stearate, polyvidone, sodium carboxymethylcellulose, hydroxypropylmethylcellulose, polysorbate, talc, and titanium dioxide.

Diclofenac potassium 50 mg film-coated tablets marketed variously as Cataflam,® Voltfast,® and Voltaren® Rapid contain calcium phosphate, saccharose, maize starch, talc, sodium carboxymethylcellulose, colloidal anhydrous silica, polyvinylpyrrolidone, microcrystalline cellulose, magnesium stearate, polyethylene glycol, titanium dioxide, and iron oxide red.

Diclofenac potassium 12.5 mg film-coated tablets marketed as Voltaren Dolo® contain colloidal anhydrous silica, lactose, maize starch, sodium starch glycolate, polyvidone, magnesium stearate, microcrystalline cellulose, hydroxypropylmethylcellulose, titanium dioxide, macrogol, polysorbate 80, and maltodextrin.

Diclofenac free acid 46.5 mg dispersible tablets (equivalent to 50 mg as sodium salt) marketed as Voltarol® contain microcrystalline cellulose, croscarmellose sodium, sodium starch glycollate, sodium saccharin, cellulose, hydrogenated castor oil, talc, silicon dioxide, erythrosine, aluminium oxide, and blackcurrant flavor.

Each of these commercially marketed products employ traditional disintegrants such as croscarmellose sodium, crospovidone and sodium starch glycolate to aid in the break up of the compacted mass and expose the active ingredient to the solvent. The formulations are not designed to expose the active ingredient by dissolving the excipient base. Even the diclofenac potassium product marketed as Voltfast, which is marketed based on its fast onset of action, contains excipients such as calcium phosphate that are practically insoluble. While Voltfast® does contain saccharose, which is very soluble in water, this ingredient is only present only in a minor amount in the outer film coating.

Mannitol is a water soluble, non-hygroscopic diluent that produces a semi-sweet, smooth, cool taste, that has been used for in chewable tablet formulations prepared by direct compression and orally disintegrating tablets (ODTs). Sangekar et al., J. Pharm. Sci., vol. 61, pp. 939-944 (1972). Joshi et al. report that mannitol is often preferred over lactose because of its low hygroscopicity, drug compatibility, compressibility, sweetness, and relatively slower dissolution kinetics. Joshi et al., Pharmaceutical Technology (June 2004).

Adkin et al. studied the effect of different concentrations of mannitol in solution on small intestinal transit, in Pharmaceutical Research, Vol. 12, No. 3 (1995) and Jnl. Pharm. Sci., Vol. 84, No. 12 (1995), and determined that mannitol reduced the transit time through the small intestine for solutions containing mannitol. According to the authors, this reduced transit time had a significant potential for reduced biological uptake, especially for drugs absorbed through the small intestine such as cimetidine.

SUMMARY OF THE INVENTION

The present invention provides various methods for enhancing the bioavailability of tablet and capsule dosage forms of diclofenac by employing in the formulation gas forming alkaline buffering agents, hygroscopic excipients, freely soluble diluents, wetting agents, and combinations of the foregoing, that are especially useful in the treatment of acute pain where rapid onset of relief is desired. The formulations are rapidly bioavailable, and can generally be characterized by (i) a disintegration time of less than about 15 minutes when tested according to USP 28 <701>, (ii) a $t_{max}$ of from about 15 to about 40 minutes, and (iii) a $C_{max}$ of from about 1500 to about 2500 ng/ml for a 50 mg dose, normalized to from about 0.03 liter$^{-1}$ to about 0.05 liter$^{-1}$.

Therefore, in one embodiment the invention provides a method of treating pain comprising orally administering diclofenac potassium in an intact rapidly bioavailable tablet or capsule dosage form characterized by (i) a $t_{max}$ of from about 10 to about 30 minutes, (ii) a $C_{max}$ of from about 1700 to about 2500 ng/ml for a 50 mg. dose, and preferably (iii) a disintegration or dissolution time of less than about 15 minutes when tested according to USP 28 <701> or USP 28 <711>, wherein the dosage form meets one or more of the following conditions:

- the dosage form comprises means for generating a gaseous and alkaline environment for said diclofenac potassium when orally ingested into the stomach.
- the dosage form comprises from about 5 to about 25 wt. % of a hygroscopic excipient.
- the dosage form has a hygroscopicity of greater than about 1% water absorption at relative humidity of 80% (RH=80%) in less than 24 hrs.
- the dosage form comprises at least 25 wt. % of excipients that are freely soluble in water.
- the dosage form comprises a wetting agent/surfactant.
- the dosage form comprises from about 35 to about 80 wt. % of a hygroscopic diluent and a freely soluble diluent at a weight ratio of from about 1:20 to about 5:1.
- the dosage form is a tablet that disintegrates faster as the hardness of the tablet increases.
- the dosage form observes only one peak concentration when ingested orally.
- a coefficient of variation in observed $C_{max}$ values of less than about 60%.

In further embodiments, the invention provides tablet and capsule dosage forms meeting the foregoing characteristics, and methods of manufacturing such tablets and capsules using wet and dry granulation techniques, alcoholic and aqueous granulation, and direct tablet compression.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE PREFERRED EMBODIMENTS

Definitions

Figure 1:
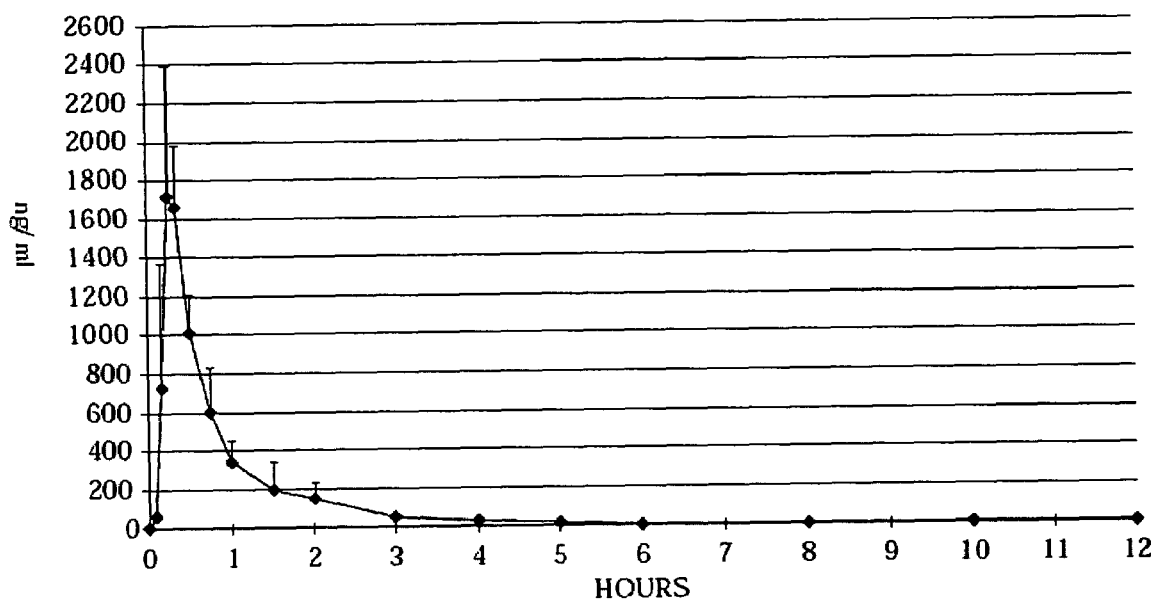
FIG. 1 is a graphical depiction of the mean plasma concentration-time profile of diclofenac measured after oral administration of the $T_1$ formulation.
Figure 2:
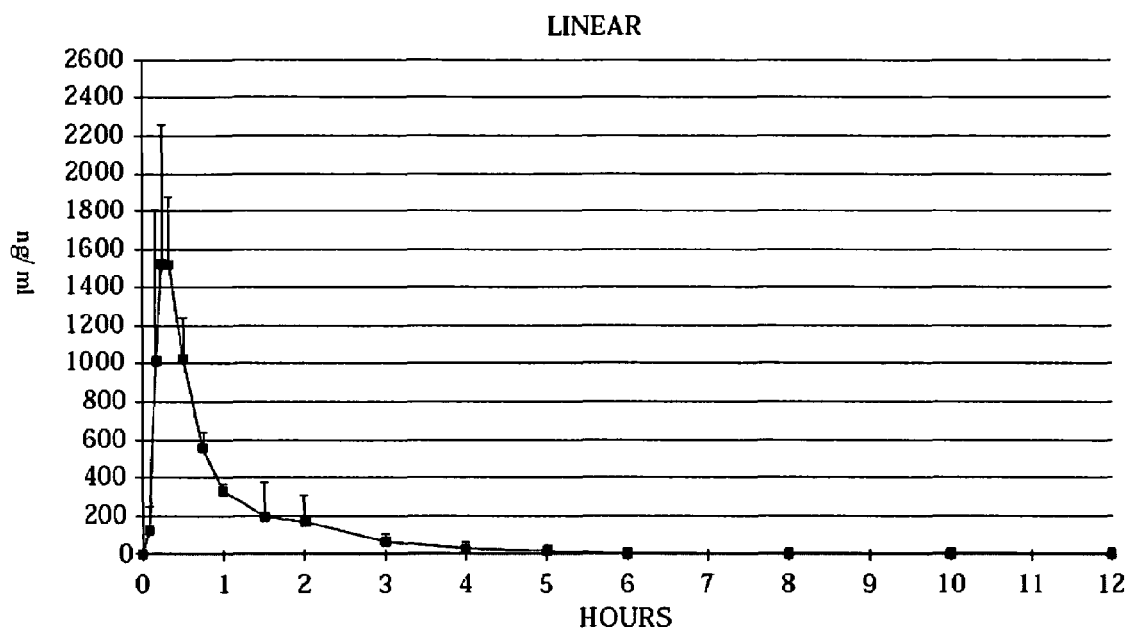
FIG. 2 is a graphical depiction of the mean plasma concentration-time profile of diclofenac measured after oral administration of the $T_2$ formulation.

As used in the specification and claims, the singular forms a, an and the include plural references unless the context clearly dictates otherwise. For example, the term a pharmaceutical excipient may refer to one or more pharmaceutical excipients for use in the presently disclosed formulations and methods.

USP means the United States Pharmacopeia and National Formulary (USP 28-NF 23). Rockville, Md.: United States Pharmacopeia Convention; 2004, unless stated to the contrary. USP 28 <701> refers to physical test 701, disintegration, contained on pages 2411-2412 of the USP.

A dosage form, as used herein, refers to a formulation that is ready for administration to a subject. As used herein, it specifically refers to solid dosage forms, including, but not limited to, tablets, powders and capsules. An "intact" dosage form refers to a dosage form which is ingested in the form it is provided. Intact dosage forms are therefore to be distinguished from orally disintegrating tablets which disintegrate in the mouth before being ingested, or effervescent tablets which are dissolved in water before being ingested.

$C_{max}$ refers to the maximum plasma concentration of a drug following the oral administration of the solid oral dosage form to patients. Normalized $C_{max}$ refers to the value obtained by dividing $C_{max}$ into the dosage strength of the solid oral dosage form.

AUC refers to the area under the curve that tracks the plasma concentration (ng/ml) of a drug over a given time following the oral administration of the solid oral dosage form to patients. AUC can be measured from 0 to 12 hours or from 0 to 24 hrs following the administration and in these cases are referred to as AUC ((0-12)) or AUC ((0-24)), respectively.

Normalized AUC is obtained by dividing the AUC into the dosage strength of the solid oral dosage form of the drug. For example, if the AUC ((0-12)) is 160 hr·ng/ml following the oral administration of a solid oral dosage form containing 200 mg of active ingredient, the normalized AUC ((0-12)) is 0.8 hr·ng/ml/mg.

Diclofenac is chemically described as [(2,6-dichloro-anilino)-2-phenyl]-2-acetic acid, and is represented by the following chemical structure:

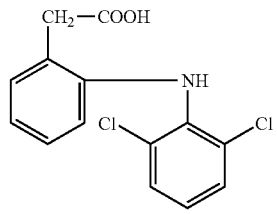

When used herein, the term diclofenac means the acetic acid form of diclofenac, and any of its pharmaceutically acceptable salts. Therefore, when a weight ratio is given, it will be understood that the ratio refers to the relative weight of diclofenac acid in the ratio, and the relative weight of diclofenac potassium (or other salt) in the ratio.

As discussed above, the invention provides (i) methods for treating pain using diclofenac potassium, (ii) dosage forms of diclofenac potassium that are useful for treating pain, and (iii) methods of manufacturing such dosage forms. Although the compositions of the present invention are useful in chronic pain conditions such as rheumatoid arthritis, osteoarthritis, and ankylosing spondylitis; and periarticular disorders such as bursitis and tendonitis; they are particularly useful in the treatment of acute pain conditions, including soft tissue disorders such as sprains and strains, migraine attacks, and other painful conditions such as renal colic, acute gout, dysmenorrhoea, and following some surgical procedures.

Therefore, in one embodiment the invention provides a method of treating pain comprising orally administering diclofenac potassium in an intact tablet or capsule dosage form characterized by (i) a $t_{max}$ of from about 10 to about 30 minutes, (ii) a $C_{max}$ of from about 1700 to about 2500 ng/ml for a 50 mg. dose, and preferably (iii) a disintegration or dissolution time of less than about 15 minutes when tested according to USP 28 <701> or USP 28 <711>, wherein the dosage form meets one or more of the following conditions:

- the dosage form comprises means for generating a gaseous and alkaline environment for said diclofenac potassium when orally ingested into the stomach.
- the dosage form comprises from about 5 to about 25 wt. % of a hygroscopic excipient.
- the dosage form has a hygroscopicity of greater than about 1% water absorption at relative humidity of 80% (RH=80%) in less than 24 hrs.
- the dosage form comprises at least 25 wt. % of excipients that are freely soluble in water.
- the dosage form comprises a wetting agent/surfactant.
- the dosage form comprises from about 35 to about 80 wt. % of a hygroscopic diluent and a freely soluble diluent at a weight ratio of from about 1:20 to about 5:1.
- the dosage form is a tablet that disintegrates faster as the hardness of the tablet increases.
- the dosage form observes only one peak concentration when ingested orally.
- a coefficient of variation in observed $C_{max}$ values of less than about 60%.

In further embodiments, the invention provides tablet and capsule dosage forms meeting the foregoing characteristics, and methods of manufacturing such tablets and capsules using wet and dry granulation techniques, alcoholic and aqueous granulation, and direct tablet compression.

$t_{max}$

Mean $t_{max}$ attained by the formulations of the present invention is preferably less than about 40 minutes, 35 minutes, 30 minutes, 25 minutes or 20 minutes, and greater than about 5 minutes, 10 minutes or 15 minutes. Mean $t_{max}$ is preferably from about 5 to about 30 minutes, or from about 13 to about 27 minutes.

Furthermore, the $t_{max}$ of the formulations of the present invention show a coefficient of variation which is about 44-86% lower than presently marketed formulations. (The corresponding coefficient of variation is normally in the range of 70-90%, which means that the $T_{max}$ is strongly variable and dependent on the physical characteristics of the patient (Physicians' Desk Reference, 52 edition, 1998, pag. 1831)). The inter-subject coefficient of variability for said $t_{max}$ is preferably less than about 80, 75, 70, 60, 50, 49, 46, 40, 35, 30% or 25%.

$C_{max}$

Mean $C_{max}$ attained by the formulations of the present invention is preferably greater than about 1400 ng/ml (0.028 liter$^{-1}$), 1500 ng/ml (0.03 liter$^{-1}$), 1600 ng/ml (0.032 liter$^{-1}$) or 1700 ng/ml (0.034 liter$^{-1}$), and less than about 2500 ng/ml (0.05 liter$^{-1}$) or 2300 ng/ml (0.046 liter$^{-1}$), for a 50 mg. formulation. A preferred range is 1700-2500 or 1700-2300 ng/ml for a 50 mg. formulation. In contrast to other commercially marketed diclofenac formulations, the formulations of the present invention preferably display only one meaningful peak blood concentration after ingestion. The inter-subject coefficient of variability for said $C_{max}$ preferably is less than about 70, 60, 50, 45 or 40%.

Figure 3:
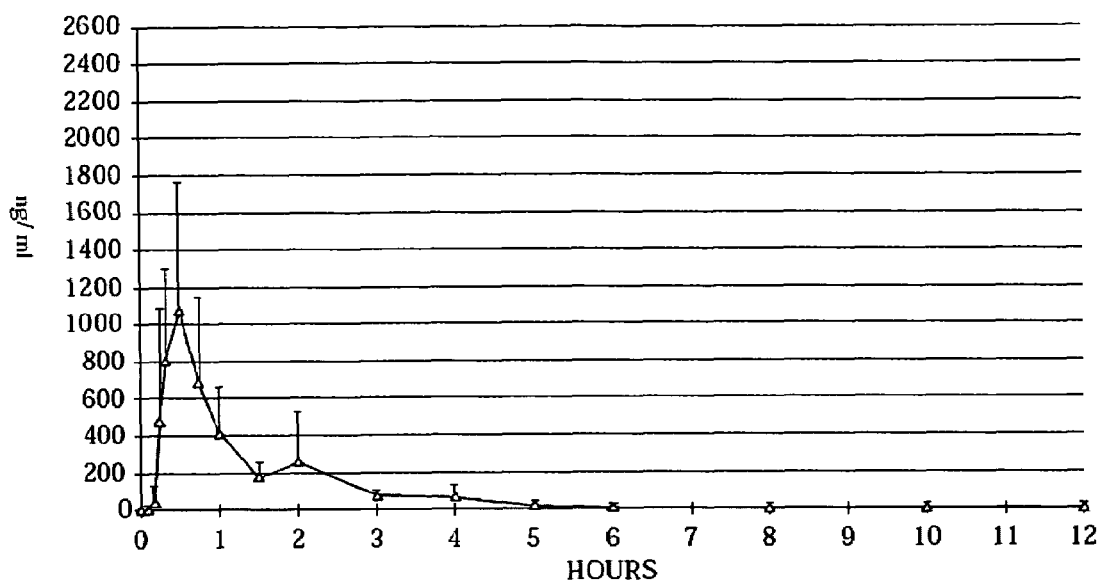
FIG. 3 is a graphical depiction of the mean plasma concentration-time profile of diclofenac measured after oral administration of the R (Voltarene Rapide™) formulation.
Figure 4:
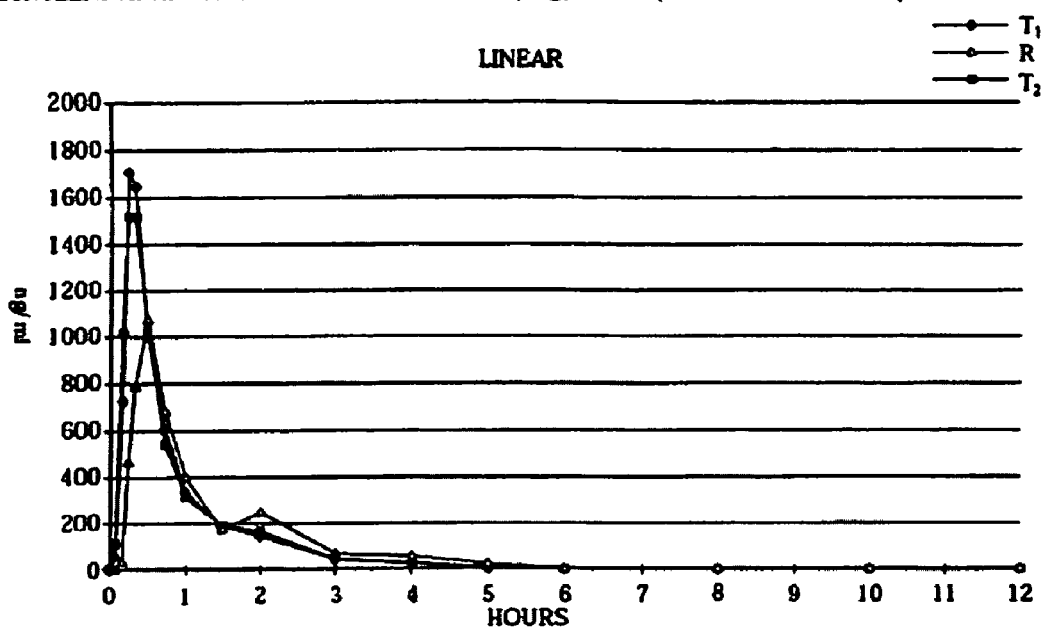
FIG. 4 is a graphical overlay of the mean plasma concentration-time profile of diclofenac measured after oral administration of the $T_1$, $T_9$ and R formulations.

In addition, the $C_{max}$ observed for the formulations of the present invention preferably demonstrate only one concentration peak when $C_{max}$ is plotted against time. As can be seen by comparing the formulations of the present invention (FIG. 1) with a prior art diclofenac potassium formulation (FIG. 3), the rapid and discreet absorption of diclofenac potassium through the gastrointestinal tract and into the bloodstream, when formulated according to the present invention, yields a $C_{max}$ curve that demonstrates only one meaningful peak.

Preferred $C_{max}$ and $t_{max}$ ranges for various dosage forms of the invention are set forth below in Table A:

TABLE A

| | Mean $C_{max}$ (ng/ml) | Mean $t_{max}$ (min) |
| --- | --- | --- |
| 50 mg. diclofenac tablet or capsule | 1500-2100; 1750-2000; 1600-1900 | 5-35; 10-30; 12-25; 15-20 |
| 25 mg. diclofenac tablet or capsule | 700-1150; 750-950; 800-900; 850-1050; 900-1000 | 5-35; 10-30; 15-30; 15-25 |
| 12.5 mg. diclofenac tablet or capsule | 350-650; 400-600; 450-550 | 5-35; 10-30; 15-25 |

Disintegration Time Time (USP 28 <701>)

Disintegration times for the dosage forms of the present invention, when tested according to USP 28 <701>, are preferably less than about 20 minutes, 15 minutes, 10 minutes, 5 minutes, or even 4 minutes, and greater than about 1, 2 or 3 minutes, most preferably from about 3 to about 5 minutes. In one particular embodiment, the dosage form is a tablet, and the tablet has a disintegration time that increases as the hardness of the tablet decreases. In another embodiment, the tablet has a disintegration time that increases as the moisture absorption by the tablet increases.

Dissolution Time (USP 28 <711>)

Dissolution times for the dosage forms of the present invention, when tested according to USP 28 <711>, based on the time it takes to dissolve 90 or 95 wt. % of the drug substance, are preferably less than about 20 minutes, 15 minutes, 10 minutes, 5 minutes, or even 3 minutes, and greater than about 1 or 2 minutes. In a preferred embodiment the dissolution profile of the dosage forms of the present invention is as follows: not less than 85, 90 or 95% after 15 minutes in simulated intestinal fluid (i.e. water) at pH=6.8.

Means for Generating a Gaseous and Alkaline Environment

In one embodiment the dosage forms of the present invention comprise means for generating a gaseous and alkaline environment for said diclofenac potassium when orally ingested into the stomach. Suitable means for generating a gaseous and alkaline environment that is not harmful to the gastrointestinal mucosa. These include, but are not limited to, sodium carbonate, potassium carbonate, sodium bicarbonate, potassium bicarbonate, calcium carbonate, magnesium carbonate, sodium glycine carbonate, disodium hydrogen phosphate, sodium dihydrogen phosphate, and mixtures thereof. Suitable gas generating means are not limited to those which are based upon a reaction which forms carbon dioxide. Reactants which evolve oxygen or other gases and which are safe for human consumption are also considered within the scope of the present invention.

The means for generating an alkaline and gaseous environment are typically employed in a weight ratio relative to the diclofenac of greater than about 1:5, 2:5, 2:1, 3:1 or 5:1. If desired, an upper limit on the buffer:diclofenac ratio can be placed at about 20:1, 10:1, 5:1, 1:1, 4:5 or 3:5. Ranges can be selected from any two of the foregoing values that are mathematically possible. In a preferred embodiment, the buffer:diclofenac weight ratio ranges from about 1:5 to about 4:5.

The hygroscopic excipient is typically employed in a weight ratio relative to the diclofenac of greater than about 1:5, 2:5, 2:1, 3:1 or 5:1. If desired, an upper limit on the excipient:diclofenac ratio can be placed at about 20:1, 10:1, 5:1, 1:1, 4:5 or 3:5. Ranges can be selected from any two of the foregoing values that are mathematically possible. In a preferred embodiment, the excipient:diclofenac weight ratio ranges from about 1:5 to about 4:5. As a total percentage of the dosage form, the means for generating a gaseous and alkaline environment preferably makes up greater than about 5, 7 or 9 wt. % of the dosage form formulation, and less than about 25, 20 or 15 wt. % of the formulation. The means preferably yields a pH greater than about 7.0, 7.5, 7.8 or 8.0, and less than about 9.2, 9.0, 8.8 or 8.5 when the dosage form is mixed with 50 ml of water at 25 degrees Celsius. Alternatively, the means preferably yields a pH greater than about 6.8, 7.0, 7.2, or 7.5, and less than about 8.8, 8.5, 8.3 or 8.0 when the dosage form is mixed with 200 ml of water at 25 degrees Celsius.

The results of pH testing in different quantities of water are reported below in Table B:

TABLE B

|  | pH in 50 ml | pH in 100 ml | pH in 200 ml |
| --- | --- | --- | --- |
| Diclofenac potassium 50 mg tablets | 8.43 | 8.33 | 7.95 |
| Diclofenac Potassium 50 mg capsules | 8.07 | 8.02 | 7.72 |

Hygroscopic Excipients

In a second principal embodiment the invention provides a method of treating acute pain comprising orally administering diclofenac potassium in an intact rapidly bioavailable tablet or capsule dosage form, wherein said dosage form comprises from about 5 to about 25 wt. % of a hygroscopic excipient.

There are many methods of quantitative evaluation of hygroscopicity of solid products without measuring the hygroscopic point. The most widely used method for measuring the hygroscopicity of a material is based on measuring the weight gain of a solid sample in a humidity chamber. Products that at relative humidity of 80% (RH=80%) demonstrate low water absorption ability (lower than 1% during 24 hrs) have a hygroscopic point below 80% (j<80% RH) and are not considered hygroscopic within the meaning of this invention. A hygroscopic excipient could thus have the ability to absorb greater than about 1 wt. %, 3 wt. %, 5 wt. % or 7 wt. % moisture within a twenty four hour period in a humidity chamber maintained at 80% RH and 25° C. Alternatively, a hygroscopic excipient could be defined as an excipient that is able to absorb greater than about 0.75 wt. %, 1 wt. %, 2 wt. %, 3 wt. % or 4 wt. % moisture within a twenty four hour period in a humidity chamber maintained at 60% RH and 25° C.

Various hygroscopic excipients could be used in practicing the present invention, including various water-soluble hygroscopic polyhydroxy compounds or esters thereof such as glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Other examples of hygroscopic or water-swellable materials include pharmaceutically acceptable disintegrants such as fumed silica, silica gel, crosslinked polyvinylpyrrolidone, starch NF, hygroscopic sugar and ion exchange resins. In a preferred embodiment the hygroscopic excipient is potassium bicarbonate or sodium bicarbonate.

The hygroscopic excipient is typically employed in a weight ratio relative to the diclofenac of greater than about 1:5, 2:5, 2:1, 3:1 or 5:1. If desired, an upper limit on the excipient:diclofenac ratio can be placed at about 20:1, 10:1, 5:1, 1:1, 4:5 or 3:5. Ranges can be selected from any two of the foregoing values that are mathematically possible. In a preferred embodiment, the excipient:diclofenac weight ratio ranges from about 1:5 to about 4:5. As a total percentage of the dosage form, the hygroscopic excipient preferably makes up greater than about 5, 7 or 9 wt. % of the dosage form formulation, and less than about 25, 20 or 15 wt. % of the formulation.

Hygroscopic Dosage Forms

In a third principal embodiment the invention provides a method of treating acute pain comprising orally administering diclofenac potassium in an intact rapidly bioavailable hygroscopic tablet or capsule dosage form. Once again, there are many methods of quantitative evaluation of hygroscopicity. In the present invention, dosage forms that at relative humidity of 80% (RH=80%) demonstrate low water absorption ability (lower than 1% during 24 hrs) have hygroscopic point below 80% (j<80% RH) and are not hygroscopic at normal conditions. A hygroscopic dosage form could thus have the ability to absorb greater than about 1 wt. %, 1.25 wt. %, 1.5 wt. % or 2 wt. % moisture within a twenty four hour period in a humidity chamber maintained at 80% RH and 25° C. Alternatively, a hygroscopic dosage form could be defined as a dosage form that is able to absorb greater than about 0.50 wt. %, 0.75 wt. %, 1 wt. %, 1.25 wt. %, or 1.5 wt. % moisture within a twenty four hour period in a humidity chamber maintained at 60% RH and 25° C.

Tests performed on 50 mg. diclofenac potassium tablets of the present invention maintained at 25° C. and 60% RH over twenty four hours showed an increase in KF (% water) from 1.995% (at time zero) to 3.456% (after 24 hours). Tests performed on 50 mg. diclofenac potassium capsules of the present invention maintained at 25° C. and 60% RH over twenty four hours showed an increase in KF (% water) from 1.905% (at time zero) to 2.93% (after 24 hrs.).

Freely Soluble Excipients

In a fourth principal embodiment the invention provides a method of treating acute pain comprising orally administering diclofenac potassium in an intact rapidly bioavailable tablet or capsule dosage form, wherein said dosage form comprises at least 20 wt. %, 30 wt. %, 40 wt. %, 50 wt. %, or 60 wt. % of excipients that are freely soluble in water, or greater. An excipient is considered freely soluble in the context of this application if 1 part of excipient is soluble in 1-10 parts of water at 20° C.

Examples of freely soluble excipients thus include mannitol, dextrates (i.e. a purified mixture of saccharides resulting from the controlled enzymatic hydrolysis of starch), dextrin, dextrose, fructose, lactilol, lactose anhydrous, sorbitol, sucrose, and compressible sugar. Of these, mannitol and lactilol are particularly preferred due to their beneficial non-hygroscopic properties, which improves their processing and handling during the manufacturing process.

In one embodiment the invention is defined by the combined weight percentage of hygroscopic and freely soluble diluents in the dosage form, and the weight ratio of hygroscopic diluent to freely soluble diluent. In a preferred embodiment the dosage form will comprise from about 30 to about 80 wt. % of the combined hygroscopic diluent and freely soluble diluent, from about 35 to about 75 wt. % of the combined hygroscopic diluent and freely soluble diluent, or from about from about 40 to about 70 wt. % of the combined hygroscopic diluent and freely soluble diluent. In addition, the hygroscopic diluent and freely soluble excipient will preferably be present in a weight ratio of from about 1:20 to about 5:1, from about 1:10 to about 3:1, from about 1:8 to about 1:1, from about 1:8 to about 1:2, or from about 1:4 to about 1:1.

Wetting Agents

In another principal embodiment the invention provides a method of treating acute pain comprising orally administering diclofenac potassium in an intact rapidly bioavailable tablet or capsule dosage form, wherein said dosage form comprises a wetting agent or surfactant. Surfactants which may be used in the present invention generally include all pharmaceutically-acceptable surfactants, although preferred surfactants will have an HLB value of at least 10 or 12, and preferably at least about 14 or 15. In certain preferred embodiments, the HLB value of the surfactant is from about 15 to 60, and in further embodiments is most preferably from about 16 to about 50. Suitable pharmaceutically-acceptable anionic surfactants include, for example, those containing carboxylate, sulfonate, and sulfate ions. Those containing carboxylate ions are sometimes referred to as soaps and are generally prepared by saponification of natural fatty acid glycerides in alkaline solutions. The most common cations associated with these surfactants are sodium, potassium, ammonium and triethanolamine. The chain length of the fatty acids typically range from 12 to 18. Although a large number of alkyl sulfates are available as surfactants, one particularly preferred surfactant is sodium lauryl sulfate, which has an HLB value of about 40. Other suitable wetting agents include glyceryl monooleate, sorbitan ester, docusate sodium, and cetrimide.

Diclofenac Potassium

While diclofenac acid or any of diclofenac's pharmaceutically acceptable salts could be used when practicing the current invention, diclofenac potassium is preferred. Other pharmaceutically acceptable salts include those of sodium and other alkali and alkaline earth metals, or salts of organic nature, such as the salts of basic amino acids, such as lysine, arginine and omithine. In a preferred embodiment, 10-60 mg. or 50 mg. of diclofenac potassium is used in the final dosage form, although other amounts could be used including 12.5, 25, 37.5, 75 or 100 mg. The amount of diclofenac potassium preferably does not vary by more than about 95-105% among unit dosage forms.

In general, the raw material will be a powder that exhibits no more than 0.5 wt. % loss on drying, and in which not less than 90% of the particles are less than 500 micrometers in diameter, not less than 40% and not more than 70% of the particles are less than 200 micrometers in diameter, not less than 35% and not more than 65% of the particles are less than 150 micrometers in diameter, and not less than 30% of the particles are less than 100 micrometers in diameter. In another embodiment, not less than 95% of the particles are less than 500 micrometers in diameter, not more than 90% are less than 250 micrometers in diameter, not more than 60% are less than 180 micrometers in diameter, and not more than 30% are less than 125 micrometers. (Analyses performed using sieves according to the Sieve Test 2.9.12 Eur. Ph.—Alpine Air Jet Sieve.) The average particle size for the diclofenac powder is preferably about 150, 160, 170, 180, 190, 200, 210, 220, 230, or 240 micrometers, and can range between any two of the foregoing variables (i.e. from about 150 to about 230 micrometers, or from about 170 to about 220 micrometers).

As it will be clear from the examples, the immediate release formulations for oral use of the present invention containing from 10 to 60 mg of diclofenac in acid and/or salt form together with alkali metal bicarbonates or mixtures thereof in amounts of from 20 to 80% by weight based on the weight of diclofenac permit to generate in human patients an average $C_{max}$ of diclofenac comprised between 400 and 2500 ng/ml independently on the age, sex or weight of the patients themselves. In addition, the formulations according to the present invention yield average an $t_{max}$ of Diclofenac in humans within 5-30 minutes of administration, generally 13-27, independently of the amount of diclofenac contained therein and also independently on the age, sex, weight of the patient.

Furthermore, the $t_{max}$ of the formulations of the present invention show a coefficient of variation which is lower than the presently marketed formulations; this is evidently an extremely important result from the clinical point of view as it is now possible to have a therapeutic effect of diclofenac which is foreseeable, reproducible and independent of the sex, weight and health conditions of the patient. Thus, the presently claimed diclofenac-based formulations permit to achieve a higher $C_{max}$ in a shorter $t_{max}$ and with a lower coefficient of variation when compared to the formulations available on the market, with therapeutic advantages which do not need to be commented.

EXAMPLES

Example 1

50 mg. Diclofenac K Tablet Comparison

Test Formulations: T1: Diclofenac potassium 50 mg film-coated tablets, alcohol granulation T2: Diclofenac potassium 50 mg film-coated tablets, dry granulation Reference Formulation: Diclofenac potassium, 50 mg film-coated tablets, Voltarene® Rapid by Novartis Pharma Study design: Single dose, 3-way, crossover randomised on 6 healthy volunteers Blood samples drawn: 0 (pre-dose), 5, 10, 15, 20, 30, 45, 60, 90 min, 2, 3, 4, 5, 6, 8, 10, 12 h Assay: LC-MS-MS//LOQ 5 ng/ml

TABLE 1

Formulation of Comparison Tablets

|  | T1, K salt, 50 mg, tablets | T2, K salt, 50 mg, tablets | Reference, K salt, 50 mg, Voltaren ® Rapid tablets |
|---|---|---|---|
| Description | Diclofenac potassium 50 mg film-coated tablets (by alcoholic granulation) | Diclofenac potassium 50 mg film-coated tablets (by direct compression) | Diclofenac potassium 50 mg film-coated tablets |
| Active ingredient | Diclofenac potassium mg 50 | Diclofenac potassium mg 50 | Diclofenac potassium mg 50 |
| Excipients | Potassium bicarbonate mg 22<br>Mannitol mg 50<br>Maize starch mg 25<br>Hydroxypropylmethylcellulose mg 0.2<br>Sodium laurylsulfate mg 0.1<br>Polyvinylpyrrolidone mg 1<br>Sodium starch glycollate mg 2.5<br>Magnesium stearate mg 4.5<br>Silicium aerosil FK 160 mg 1<br>Coating Opadry Clear (HPMC 2910 and polyethyleneglycol 400) mg 4 | Potassium bicarbonate mg 22<br>Mannitol 400 mg 119.9<br>Sodium laurylsulfate mg 0.1<br>Polyvinylpyrrolidone mg 6<br>Magnesium stearate mg 2<br>Film Coating Opadry Clear (HPMC 2910, polyethyleneglycol 400) mg 4 | Calcium phosphate<br>Saccharose<br>Maize starch<br>Talc<br>Sodium carboxymethylcellulose<br>Colloidal anhydrous silicium<br>Polyvinylpyrrolidone<br>Microcrystalline cellulose<br>Magnesium stearate<br>Polyethylenglycole<br>Titanidioxide (E171)<br>Iron oxide red (E172) |
| Total weight | 160.3 mg | 204 mg | |

TABLE 2

Pharmacokinetics of Comparison Tablets.

| | | PK results | | |
|---|---|---|---|---|
| | | Test 1 (K, tablets 50 mg) | Test 2 (K, tablets 50 mg) | Reference (K, tablets 50 mg) |
| $C_{max}$ | Mean | 1873.30 | 1744.8 | 1307.0 |
| | SD | 553.80 | 572.3 | 558.4 |
| | CV % | 29.5 | 32.8 | 42.7 |
| | Min | 1228.9 | 1057.4 | 581.8 |
| | Max | 2516.5 | 2468.9 | 1935.5 |
| AUC | Mean | 1219 | 1237 | 1168 |
| | SD | 246 | 276 | 282 |
| | CV % | 20.2 | 22.3 | 24.1 |
| | Min | 874 | 848 | 913 |
| | Max | 1615 | 1668 | 1642 |
| $t_{max}$ | Mean | 0.31 h (18.6 min) | 0.28 h (16.8 min) | 0.68 h (40.8 min) |
| | SD | 0.04 | 0.07 | 0.65 |
| | CV % | 12.9 | 25.0 | 95.6 |
| | Min | 0.25 h (15 min) | 0.17 h (10.2 min) | 0.25 h (15 min) |
| | Max | 0.33 h (19.8 min) | 0.33 h (19.8 min) | 2.00 h (120 min) |

Example 2

50 and 25 mg. Diclofenac K Tablet Comparison

Test Formulations: T1: Diclofenac potassium 25 mg film-coated tablets

T2: Diclofenac potassium 50 mg film-coated tablets

Reference Formulation: Diclofenac potassium, 50 mg film-coated tablets, Voltarene® Rapid by Novartis Pharma Study design: Single dose, 3-way, crossover randomised on 24 healthy volunteers Blood samples drawn: 0 (pre-dose), 5, 10, 15, 20, 30, 45, 60, 90 min, 2, 3, 4, 5, 6, 8, 10, 12 h Assay: LC-MS-MS//LOQ 5 ng/ml

TABLE 3

Formulation of Comparison Tablets

|  | T1, K salt, 25 mg, tablets | T2, K salt, 50 mg, tablets | Reference, K salt, 50 mg, Voltaren ® Rapid tablets |
|---|---|---|---|
| Description | Diclofenac potassium 25 mg film-coated tablets | Diclofenac potassium 50 mg film-coated tablets | Diclofenac potassium 50 mg film-coated tablets |
| Active ingredient | Diclofenac potassium mg 25 | Diclofenac potassium mg 50 | Diclofenac potassium mg 50 |
| Excipients | Potassium bicarbonate mg 11<br>Mannitol 400, mg 58.2<br>Sodium laurylsulfate mg 0.05<br>Polyvinylpyrrolidone mg 3<br>Polyethylenglycole mg 0.75<br>Magnesium stearate mg 2 | Potassium bicarbonate mg 22<br>Mannitol 400, mg 116.4<br>Sodium laurylsulfate mg 0.1<br>Polyvinylpyrrolidone mg 6<br>Polyethylenglycole mg 1.5<br>Magnesium stearate mg 4 | Calcium phosphate<br>Saccharose<br>Maize starch<br>Talc<br>Sodium carboxymethylcellulose<br>Colloidal anhydrous silicium<br>Polyvinylpyrrolidone |

TABLE 3-continued

Formulation of Comparison Tablets

|  | T1, K salt, 25 mg, tablets | T2, K salt, 50 mg, tablets | Reference, K salt, 50 mg, Voltaren ® Rapid tablets |
|---|---|---|---|
|  | Film Coating Opadry Clear (HPMC 2910, polyethyleneglycol 400) mg 2 | Film Coating Opadry Clear (HPMC 2910, polyethyleneglycol 400) mg 4 | Microcrystalline cellulose<br>Magnesium stearate<br>Polyethylenglycole<br>Titanidioxide (E171)<br>Iron oxide red (E172) |
| Total weight | 102 mg | 204 mg |  |

TABLE 4

Pharmacokinetics of Comparison Tablets

PK results

|  |  | T1 (K, tablets 25 mg) | T2 (K, film-coated tablets 50 mg) | Reference (K, tablets 50 mg) |
|---|---|---|---|---|
| $C_{max}$ | Mean | 940.2 (1880.4)* | 1766.7 | 1339.6 |
|  | SD | 387.0 | 1020.2 | 627.5 |
|  | CV % | 41.2 | 57.7 | 46.8 |
|  | Min | 228.5 | 317.3 | 336.5 |
|  | Max | 1595.4 | 4516.9 | 2655.4 |
| AUC | Mean | 611.81 (1223.63)* | 1267.67 | 1286.43 |
|  | SD | 144.76 | 356.46 | 351.22 |
|  | CV % | 23.7 | 28.1 | 27.3 |
|  | Min | 380.13 | 681.89 | 852.09 |
|  | Max | 919.81 | 2123.22 | 2185.01 |
| $t_{max}$ | Mean | 0.354 h (21.2 min) | 0.489 h (29.8 min) | 0.847 h (50.8 min) |
|  | SD | 0.119 | 0.366 | 0.887 |
|  | CV % | 33.6 | 78.8 | 104.7 |
|  | Min | 0.250 h (15 min) | 0.167 h (10 min) | 0.333 h (20 min) |
|  | Max | 0.750 h (45 min) | 1.5 h (90 min) | 4 h (240 min) |

*values normalized to the dose of 50 mg

Example 3

50 mg. Diclefenac K Tablet Comparison

Test Formulation: Diclofenac potassium 50 mg film-coated tablets
Reference Formulation: Diclofenac potassium, 50 mg film-coated tablets, Voltfast® by Novartis Pharma Study design: Single dose, 2-way, crossover randomised on 26 healthy volunteers Blood samples drawn: 0 (pre-dose), 10, 20, 30, 45, 60, 90 min, 2, 3, 4, 5, 6, 8, 10, 12 h Assay: LC-MS-MS//LOQ 3.3 ng/ml

TABLE 5

Formulation of Comparison Tablets

|  | K salt, 50 mg, tablets | Reference, K salt, 50 mg, Voltfast ® tablets |
|---|---|---|
| Description | Diclofenac potassium 50 mg film-coated tablets | Diclofenac potassium 50 mg film-coated tablets |
| Active ingredient | Diclofenac potassium mg 50 | Diclofenac potassium mg 50 |
| Excipients | Potassium bicarbonate mg 22<br>Mannitol 400, mg 116.4<br>Sodium laurylsulfate mg 0.1<br>Polyvinylpyrrolidone mg 6<br>Polyethylenglycole mg 1.5<br>Magnesium stearate mg 4<br><br>Film Coating Opadry Clear (HPMC 2910, polyethyleneglycol 400) mg 4 | Calcium phosphate<br>Saccharose<br>Maize starch<br>Talc<br>Sodium carboxymethylcellulose<br>Colloidal anhydrous silicium<br>Polyvinylpyrrolidone<br>Microcrystalline cellulose<br>Magnesium stearate<br>Polyethylenglycole<br>Titanidioxide (E171)<br>Iron oxide red (E172) |
| Total weight | 204 mg |  |

TABLE 6

Pharmacokinetics of Comparison Tablets

PK results

|  |  | Test (K, tablets 50 mg) | Reference (K, tablets 50 mg) |
|---|---|---|---|
| $C_{max}$ | Mean | 1768.6 | 1386.5 |
|  | SD | 771.6 | 693.3 |
|  | CV % | 43.6 | 50.0 |
|  | Min | 514.3 | 300.2 |
|  | Max | 3726.4 | 2744 |
| AUC | Mean | 1248 | 1220.2 |
|  | SD | 326 | 352.7 |
|  | CV % | 26.1 | 28.9 |
|  | Min | 661.8 | 609 |
|  | Max | 1918.4 | 1971.3 |
| $t_{max}$ | Mean | 0.455 h (27.3 min) | 0.904 h (54.24 min) |
|  | SD | 0.275 | 0.838 |
|  | CV % | 60.0 | 92.7 |
|  | Min | 0.166 h (10 min) | 0.333 h (20 min) |
|  | Max | 1.5 h (90 min) | 4.00 h (240 min) |

Example 4

12.5 mg. Diclofenac K Tablet Comparison

Test Formulations: Diclofenac potassium 12.5 mg film-coated tablets

Reference Formulation: Diclofenac potassium, 12.5 mg immediate release film-coated tablets, Voltaren Dolo® by Novartis Consumer Health Study design: Single dose, 2-way, crossover randomised on 24 healthy volunteers Blood samples drawn: 0 (pre-dose), 5, 10, 15, 20, 30, 45, 60, 75, 90 min, 2, 3, 4, 5, 6, 8, 12 h Assay: LC-MS-MS//LOQ 0.2 ng/ml

TABLE 7

Formulation of Comparison Tablets

|  | K salt, 12.5 mg, tablets | Reference, K salt, 12.5 mg, Voltaren Dolo ® |
|---|---|---|
| Description | Diclofenac potassium 12.5 mg film-coated tablets | Diclofenac potassium 12.5 mg film-coated tablets |
| Active ingredient | Dicbofenac potassium mg 12.5 | Diclofenac potassium mg 12.5 |
| Excipients | Potassium hydrogen carbonate mg 5.50<br>Mannitol mg 76.25<br>Sodium laurylsulfate mg 0.25<br>Glycerol dibehenate mg 1.50<br>Crospovidone mg 3.00<br>Magnesium stearate mg 1.00<br><br>Film Coating Opadry Clear (HPMC 2910 and polyethyleneglycol 400) mg 2.00 | Colloidal anhydrous silica<br>Lactose<br>Maize starch<br>Sodium starch glycollate<br>Polyvidone<br>Magnesium stearate<br>Microcrystalline cellulose<br>Hydroxypropylmethylcellulose<br>Titanidioxide (E171)<br>Macrogol<br>Polysorbate 80<br>Maltodextrin |
| Total weight | 102.00 mg |  |

TABLE 8

Pharmacokinetics of Comparison Tablets

PK results

|  |  | Test (K, tablets 12.5. mg) | Reference (K, tablets 12.5 mg) |
|---|---|---|---|
| $C_{max}$ | Mean | 494.09 | 435.80 |
|  | SD | 223.36 | 228.92 |
|  | CV % | 45.21 | 52.53 |
|  | Min | 130.50 | 162.50 |
|  | Max | 909.10 | 959.00 |
| ACU | Mean | 331.19 | 330.14 |
|  | SD | 71.42 | 84.70 |
|  | CV % | 21.56 | 25.66 |
|  | Min | 172.54 | 171.38 |
|  | Max | 435.39 | 445.72 |
| $t_{max}$ | Mean | 0.35 h (21 min) | 0.48 h (28.8 min) |
|  | SD | 0.20 | 0.35 |
|  | CV % | 57.14 | 72.92 |
|  | Min | 0.17 h (10.2 min) | 0.17 h (10.2 min) |
|  | Max | 1.0 h (60 min) | 1.50 h (90 min) |

Example 5

Diclofenac K Uncoated Tablet Comparison

A further comparative test was carried out on uncoated immediate release formulations T1 and T2, as reported in Example 1. A comparative bioavailabilty study was carried out on 6 healthy volunteers of both sexes in order to evaluate the in vivo results of the pharmacokinetic profiles of the present formulations if compared to those of a bioequivalent fast release formulation such as Voltaren Rapid® (50 mg of diclofenac potassium), by Novartis. The results, which are reported in FIGS. 1-4 are also in this case excellent: the $T_{max}$ is in fact prompter with the present formulations (T1=18.6 min, T2=16.8 min vs R1 40.8 min) and the $C_{max}$ is higher (T1=1878.3 ng/ml and T2=1744.8 ng/ml vs R1 1307 ng/ml); furthermore, also in this case the $T_{max}$ of both present formulations shows a coefficient of variation lower than reference formulation (T1=12.9% and T2=25% vs R1=95.6%).

Example 6

Tablet Core Formulations

Uncoated diclofenac tablets containing 50 mg. of diclofenac potassium were prepared based on the formulations given in Table 9 below. Formulations were prepared using alcoholic granulation (Tablet C) and direct compression (Tablet B).

TABLE 9

| Names of ingredients | Tablet C (alcoholic granulation) | Tablet B (direct compression) | Function | Standard |
|---|---|---|---|---|
| Active ingredients | | | | |
| Diclofenac potassium | 50 mg.* | 50 mg | Active ingredient | Eur. Ph. |
| Tablet cores excipients | | | | |
| Potassium hydrogen carbonate | 22 | 22 | Buffering agent | Eur. Ph. |
| Mannitol | 50 | 119.9 | Diluent and disintegrating agent | Eur. Ph. |
| Maize starch | 25 | / | Binder diluent | Eur. Ph. |
| Methocel A4C | 0.2 | / | Thichener | Eur. Ph. |
| Crospovidone | 1.0 | 6.0 | Binder | Eur. Ph. |
| Sodium lauryl sulphate | 0.1 | 0.1 | Solubilizing agent | Eur. Ph. |
| Magnesium stearate | 4.5 | 2.0 | Lubricant agent | Eur. Ph. |
| Ultramyl | 2.5 | / | Lubricant agent | Eur. Ph. |
| Aerosil | 1.0 | / | Lubricant agent | Eur. Ph. |
| Total weight | 156.3 | 200.0 mg | | |

*Units are in milligrams unless otherwise specified.

Example 7

Stability Testing

Stability tests were conducted in various blister packaging materials on the tablet cores (Tablet B and Tablet C), and on Tablet B tablets coated with an aqueous polymer coating suspension (Tablet BA) and an alcoholic polymer coating solution (Tablet BB). Stability testing was restricted to three different blister types. The properties of the forming and lidding films used in the three blister materials tested are as follows:

- PVDC-coated PVC and hard aluminum (25 μm, coated on the underside with a vinyl lacquer) are the materials of the forming film and the lidding part of the tested blister 1, respectively. The thickness of the PVDC coat is 40 μm while that of the PVC film is 250 μm.
- PVDC-coated PVC and hard aluminum (25 μm, coated on the underside with a vinyl lacquer) are the materials of the forming film and the lidding part of the tested blister 2, respectively. The thickness of the PVDC coat is 80 μm while that of the PVC film is 250 μm.
- OPA/Al/PVC and hard aluminum (25 μm, coated on the underside with a vinyl lacquer) are the materials of the forming film and the lidding part of the tested blister 3, respectively. Nylon (Oriented Polyamide)-Aluminum-PVC (OPA/Al/PVC) is a laminate, which consists of 25 μm OPA/45 μm aluminum/60 μm PVC.

An appropriate quantity of tablet cores (Tablets B and C) and coated tablets (Tablets BA and BB), in original packaging (blisters 1-3) was stored in Weiss-Enet climatic chambers for six months under the following conditions of temperature and relative humidity:

| Temperature (° C.) | Relative humidity (±1%) |
|---|---|
| 25 | 60 |
| 30 | 60 |
| 40 | 75 |

Samples were withdrawn at suitable intervals and subjected to testing for Diameter, Thickness, Hardness, Weight, Disintegration time in water (37° C.), Water content, Dissolution buffered pH 7.5 medium, and Assay. The measurements were performed on six tablet cores or coated tablets taken at random in all instances, and the average values were recorded. The results are given in Tables 10-15 below.

TABLE 10

Influence of packaging material (blisters 1, 2 and 3) on the stability of Tablets B and C stored at 25° C. (RH = 60%)[a]

| Tests | Tablet B[b] Time zero | Tablet B Blister 1[c] 3 months | | Tablet B Blister 1[c] 6 months | Tablet B Blister 2 3 months | Tablet B Blister 2 6 months | Tablet B Blister 3 3 months | Tablet B Blister 3 6 months | Tablet C[d] Time zero | Tablet C Blister 1[c,e] 3 months | Tablet C Blister 1[c,e] 6 months | Tablet C Blister 2[e] 3 months | Tablet C Blister 2[e] 6 months | Tablet C Blister 3[e] 3 months | Tablet C Blister 3[e] 6 months |
|---|---|---|---|---|---|---|---|---|---|---|---|---|---|---|---|
| Diameter[f] (mm) | 7.0 | 7.0 | | / | 7.1 | 7.1 | 7.0 | 7.1 | 7.0 | 7.0 | / | 7.0 | / | 7.0 | / |

TABLE 10-continued

Influence of packaging material (blisters 1, 2 and 3) on the stability of Tablets B and C stored at 25° C. (RH = 60%)[a]

| Tests | Tablet B[b] Time zero | Tablet B Blister 1[c] 3 months | Tablet B Blister 1[c] 6 months | Tablet B Blister 2 3 months | Tablet B Blister 2 6 months | Tablet B Blister 3 3 months | Tablet B Blister 3 6 months | Tablet C[d] Time zero | Tablet C Blister 1[c,e] 3 months | Tablet C Blister 1[c,e] 6 months | Tablet C Blister 2[e] 3 months | Tablet C Blister 2[e] 6 months | Tablet C Blister 3[e] 3 months | Tablet C Blister 3[e] 6 months |
|---|---|---|---|---|---|---|---|---|---|---|---|---|---|---|
| Thickness[f] (mm) | 4.4 | 4.4 | / | 4.4 | 4.5 | 4.4 | 4.4 | 3.5 | 3.6 | / | 3.5 | / | 3.5 | / |
| Hardness[f] (N) | 71 | 65 | / | 65 | 63 | 71 | 74 | 31 | 24 | / | 25 | / | 32 | / |
| Weight (mg) | 198 | 201 | / | 200 | 199 | 199 | 198 | 154 | 157 | / | 155 | / | 155 | / |
| Water content[g] (%) | 2.4 | 3.2 | / | 2.8 | 2.7 | 2.6 | 2.5 | 3.5 | 3.5 | / | 5.0 | / | 4.2 | / |
| Disintegration time[h] (min.:sec.) | 2:50 | 6:12 | / | 3:43 | 3:56 | 2:33 | 2:33 | 3:05 | 2:28 | / | 2:23 | / | 2:12 | / |
| Dissolution[i] after 20 min. (%) | 93 | 96 | / | 98 | 96 | 95 | 99 | 95 | 96 | / | 98 | / | 97 | / |
| Assay[j] (%) | 96.6 | 95.6 | / | 96.0 | 96.2 | 99.8 | 99.0 | 97.0 | 96.4 | / | 97.8 | / | 99.2 | / |

[a]All values are average values determined on six units taken at random.
[b]Matrix tablets produced by direct compression of the mixture F11 with a rotary tablet machine.
[c]Stability in blister 1 was interrupted after 3 months.
[d]Matrix tablets produced from the mixture F3 (alcoholic granulation) with a rotary tablet machine.
[e]Stability of batch no. 990310C was interrupted after 3 months.
[f]Erweka TBH 30 HD apparatus.
[g]Determined according to Eur. Ph. (Karl Fischer semi-micro water determination).
[h]Determined in water (37° C.) according to Eur. Ph.
[i]Determined in buffered pH 7.5 medium according to Eur. Ph.
[j]Determined by high performance liquid chromatography (HPLC).

TABLE 11

Influence of packaging material (blisters 1, 2 and 3) on the stability of Tablets B and C stored at 30° C. (RH = 60%)[a]

| Tests | Tablet B[b] Time zero | Tablet B Blister 1[c] 3 months | Tablet B Blister 1[c] 6 months | Tablet B Blister 2 3 months | Tablet B Blister 2 6 months | Tablet B Blister 3 3 months | Tablet B Blister 3 6 months | Tablet C[d] Time zero | Tablet C Blister 1[c,e] 3 months | Tablet C Blister 1[c,e] 6 months | Tablet C Blister 2[e] 3 months | Tablet C Blister 2[e] 6 months | Tablet C Blister 3[e] 3 months | Tablet C Blister 3[e] 6 months |
|---|---|---|---|---|---|---|---|---|---|---|---|---|---|---|
| Diameter[f] (mm) | 7.0 | 7.1 | / | 7.1 | 7.1 | 7.1 | 7.1 | 7.0 | 7.1 | / | 7.0 | / | 7.0 | / |
| Thickness[f] (mm) | 4.4 | 4.5 | / | 4.5 | 4.5 | 4.4 | 4.5 | 3.5 | 3.6 | / | 3.6 | / | 3.4 | / |
| Hardness[f] (N) | 71 | 66 | / | 60 | 64 | 72 | 71 | 31 | 24 | / | 27 | / | 31 | / |
| Weight (mg) | 198 | 202 | / | 200 | 202 | 199 | 199 | 154 | 158 | / | 157 | / | 154 | / |
| Water content[g] (%) | 2.4 | 6.4 | / | 3.6 | 3.1 | 2.2 | 2.5 | 3.5 | 6.4 | / | 5.7 | / | 4.0 | / |
| Disintegration time[h] (min.:sec.) | 2:50 | 5:32 | / | 5:09 | 5:49 | 2:40 | 2:30 | 3:05 | 2:17 | / | 2:09 | / | 2:35 | / |
| Dissolution[i] L after 20 min. (%) | 93 | 95 | / | 94 | 95 | 93 | 96 | 95 | 97 | / | 96 | / | 98 | / |
| Assay[j] (%) | 96.6 | 94.2 | / | 95.4 | 96.0 | 96.0 | 96.4 | 97.0 | 97.2 | / | 97.2 | / | 100.0 | / |

TABLE 12

Influence of packaging material (blisters 1, 2 and 3) on the stability of Tablets B and C stored at 40° C. (RH = 75%)[a]

| Tests | Tablet B[b] Time zero | Tablet B Blister 1[c] 3 months | Tablet B Blister 1[c] 6 months | Tablet B Blister 2 3 months | Tablet B Blister 2 6 months | Tablet B Blister 3 3 months | Tablet B Blister 3 6 months | Tablet C[d] Time zero | Tablet C Blister 1[c,e] 3 months | Tablet C Blister 1[c,e] 6 months | Tablet C Blister 2[e] 3 months | Tablet C Blister 2[e] 6 months | Tablet C Blister 3[e] 3 months | Tablet C Blister 3[e] 6 months |
|---|---|---|---|---|---|---|---|---|---|---|---|---|---|---|
| Diameter[f] (mm) | 7.0 | 7.2 | / | 7.1 | 7.1 | 7.0 | 7.1 | 7.0 | 7.1 | / | 7.0 | / | 7.0 | / |
| Thickness[f] (mm) | 4.4 | 4.5 | / | 4.5 | 4.6 | 4.6 | 4.4 | 3.5 | 3.7 | / | 3.6 | / | 3.5 | / |
| Hardness[f] (N) | 71 | 64 | / | 67 | 62 | 71 | 70 | 31 | 23 | / | 27 | / | 30 | / |
| Weight (mg) | 198 | 205 | / | 201 | 205 | 198 | 200 | 154 | 161 | / | 158 | / | 154 | / |
| Water content[g] (%) | 2.4 | 5.3 | / | 3.6 | 5.2 | 2.1 | 2.2 | 3.5 | 7.3 | / | 6.2 | / | 4.0 | / |
| Disintegration time[h] (min.:sec.) | 2:50 | 7:20 | / | 6:16 | 6:12 | 3:17 | 3:31 | 3:05 | 2:27 | / | 2:28 | / | 2:23 | / |
| Dissolution[i] after 20 min. (%) | 93 | 92 | / | 95 | 96 | 94 | 95 | 95 | 92 | / | 95 | / | 94 | / |
| Assay[j] (%) | 96.6 | 92.6 | / | 92.6 | 92.2 | 96.0 | 96.3 | 97.0 | 97.2 | / | 96.4 | / | 99.4 | / |

TABLE 13

Influence of packaging material (blisters 1, 2 and 3) on the stability of film-coated Tablets BA and BB stored at 25° C. (RH = 60%)[a]

| Tests | Tablet BA[b] Time zero | Tablet BA Blister 1[c] 3 months | Tablet BA Blister 1[c] 6 months | Tablet BA Blister 2 3 months | Tablet BA Blister 2 6 months | Tablet BA Blister 3 3 months | Tablet BA Blister 3 6 months | Tablet BB[d] Time zero | Tablet BB Blister 1[c] 3 months | Tablet BB Blister 1[c] 6 months | Tablet BB Blister 2 3 months | Tablet BB Blister 2 6 months | Tablet BB Blister 3 3 months | Tablet BB Blister 3 6 months |
|---|---|---|---|---|---|---|---|---|---|---|---|---|---|---|
| Diameter[f] (mm) | 7.1 | 7.1 | / | 7.1 | 7.1 | 7.1 | 7.2 | 7.1 | 7.1 | / | 7.1 | 7.2 | 7.1 | 7.2 |
| Thickness[f] (mm) | 4.6 | 4.6 | / | 4.5 | 4.6 | 4.5 | 4.5 | 4.5 | 4.6 | / | 4.5 | 4.7 | 4.5 | 4.5 |
| Hardness[f] (N) | 128 | 116 | / | 108 | 103 | 127 | 130 | 114 | 108 | / | 112 | 95 | 114 | 116 |
| Weight (mg) | 204 | 206 | / | 204 | 205 | 204 | 204 | 203 | 207 | / | 204 | 211 | 203 | 204 |
| Water content[g] (%) | 2.5 | 4.4 | / | 2.9 | 3.0 | 2.1 | 3.2 | 2.3 | 3.5 | / | 2.8 | 3.1 | 2.3 | 3.0 |
| Disintegration time[h] (min.:sec.) | 3:23 | 6:15 | / | 4:28 | 4:42 | 3:24 | 4:28 | 3:26 | 7:00 | / | 4:09 | 9:02 | 3:13 | 4:12 |
| Dissolution[i] after 20 min. (%) | 93 | 95 | / | 96 | 98 | 94 | 95 | 96 | 93 | / | 94 | 94 | 97 | 96 |
| Assay[j] (%) | 95.8 | 95.0 | / | 96.0 | 96.3 | 98.4 | 98.7 | 95.6 | 93.4 | / | 94.4 | 94.0 | 96.4 | 96.8 |

TABLE 14

Influence of packaging material (blisters 1, 2 and 3) on the stability of film-coated Tablets BA and BB stored at 30° C. (RH = 60%)[a]

| Tests | Tablet BA[b] Time zero | Tablet BA Blister 1[c] 3 months | Tablet BA Blister 1[c] 6 months | Tablet BA Blister 2 3 months | Tablet BA Blister 2 6 months | Tablet BA Blister 3 3 months | Tablet BA Blister 3 6 months | Tablet BB[d] Time zero | Tablet BB Blister 1[c] 3 months | Tablet BB Blister 1[c] 6 months | Tablet BB Blister 2 3 months | Tablet BB Blister 2 6 months | Tablet BB Blister 3 3 months | Tablet BB Blister 3 6 months |
|---|---|---|---|---|---|---|---|---|---|---|---|---|---|---|
| Diameter[f] (mm) | 7.1 | 7.1 | / | 7.1 | 7.1 | 7.1 | 7.1 | 7.1 | 7.1 | / | 7.1 | 7.1 | 7.1 | 7.1 |
| Thickness[f] (mm) | 4.6 | 4.6 | / | 4.5 | 4.6 | 4.5 | 4.5 | 4.5 | 4.6 | / | 4.5 | 4.6 | 4.3 | 4.6 |

TABLE 14-continued

Influence of packaging material (blisters 1, 2 and 3) on the stability of film-coated Tablets BA and BB stored at 30° C. (RH = 60%)[a]

| Tests | Tablet BA[b] Time zero | Tablet BA Blister 1[c] 3 months | Tablet BA Blister 1[c] 6 months | Tablet BA Blister 2 3 months | Tablet BA Blister 2 6 months | Tablet BA Blister 3 3 months | Tablet BA Blister 3 6 months | Tablet BB[d] Time zero | Tablet BB Blister 1[c] 3 months | Tablet BB Blister 1[c] 6 months | Tablet BB Blister 2 3 months | Tablet BB Blister 2 6 months | Tablet BB Blister 3 3 months | Tablet BB Blister 3 6 months |
|---|---|---|---|---|---|---|---|---|---|---|---|---|---|---|
| Hardness[f] (N) | 128 | 103 | / | 110 | 110 | 130 | 128 | 114 | 99 | / | 104 | 100 | 112 | 114 |
| Weight (mg) | 204 | 206 | / | 205 | 206 | 204 | 203 | 203 | 207 | / | 206 | 206 | 203 | 203 |
| Water content[g] (%) | 2.5 | 5.5 | / | 3.1 | 3.6 | 2.2 | 3.0 | 2.3 | 4.1 | / | 3.2 | 3.8 | 3.3 | 2.6 |
| Disintegration time[h] (min.:sec.) | 3:23 | 5:59 | / | 4:33 | 6:11 | 3:39 | 3:51 | 3:26 | 5:54 | / | 6:29 | 5:22 | 3:40 | 4:00 |
| Dissolution[i] after 20 min. (%) | 93 | 95 | / | 96 | 95 | 94 | 97 | 96 | 94 | / | 96 | 93 | 93 | 96 |
| Assay[j] (%) | 95.8 | 94.8 | / | 94.4 | 96.8 | 96.8 | 98.2 | 95.6 | 94.6 | / | 94.0 | 98.5 | 97.8 | 97.0 |

TABLE 15

Influence of packaging material (blisters 1, 2 and 3) on the stability of film-coated Tablets BA and BB stored at 40° C. (RH = 75%)[a]

| Tests | Tablet BA[b] Time zero | Tablet BA Blister 1[c] 3 months | Tablet BA Blister 1[c] 6 months | Tablet BA Blister 2 3 months | Tablet BA Blister 2 6 months | Tablet BA Blister 3 3 months | Tablet BA Blister 3 6 months | Tablet BB[d] Time zero | Tablet BB Blister 1[c] 3 months | Tablet BB Blister 1[c] 6 months | Tablet BB Blister 2 3 months | Tablet BB Blister 2 6 months | Tablet BB Blister 3 3 months | Tablet BB Blister 3 6 months |
|---|---|---|---|---|---|---|---|---|---|---|---|---|---|---|
| Diameter[f] (mm) | 7.1 | 7.1 | / | 7.2 | 7.2 | 7.1 | 7.1 | 7.1 | 7.2 | / | 7.1 | 7.1 | 7.1 | 7.1 |
| Thickness[f] (mm) | 4.6 | 4.6 | / | 4.6 | 4.7 | 4.5 | 4.6 | 4.5 | 4.6 | / | 4.6 | 4.6 | 4.5 | 4.6 |
| Hardness[f] (N) | 128 | 102 | / | 110 | 104 | 130 | 125 | 114 | 93 | / | 102 | 99 | 115 | 111 |
| Weight (mg) | 204 | 209 | / | 207 | 210 | 204 | 204 | 203 | 210 | / | 208 | 204 | 204 | 203 |
| Water content[g] (%) | 2.5 | 5.3 | / | 4.2 | 5.0 | 2.2 | 2.7 | 2.3 | 5.2 | / | 4.2 | 5.6 | 3.1 | 3.6 |
| Disintegration time[h] (min.:sec.) | 3:23 | 7:18 | / | 6:51 | 6:48 | 3:50 | 3:30 | 3:26 | 9:16 | / | 6:45 | 4:18 | 4:15 | 3:16 |
| Dissolution[i] after 20 min. (%) | 93 | 93 | / | 94 | 96 | 95 | 96 | 96 | 94 | / | 95 | 96 | 97 | 96 |
| Assay[j] (%) | 95.8 | 95.0 | / | 95.4 | 98.1 | 98.2 | 96.3 | 95.6 | 94.0 | / | 95.6 | 96.7 | 98.0 | 95.2 |

Example 8

Diclofenac K Tablet Dissolution Profile Comparison

Figure 5:
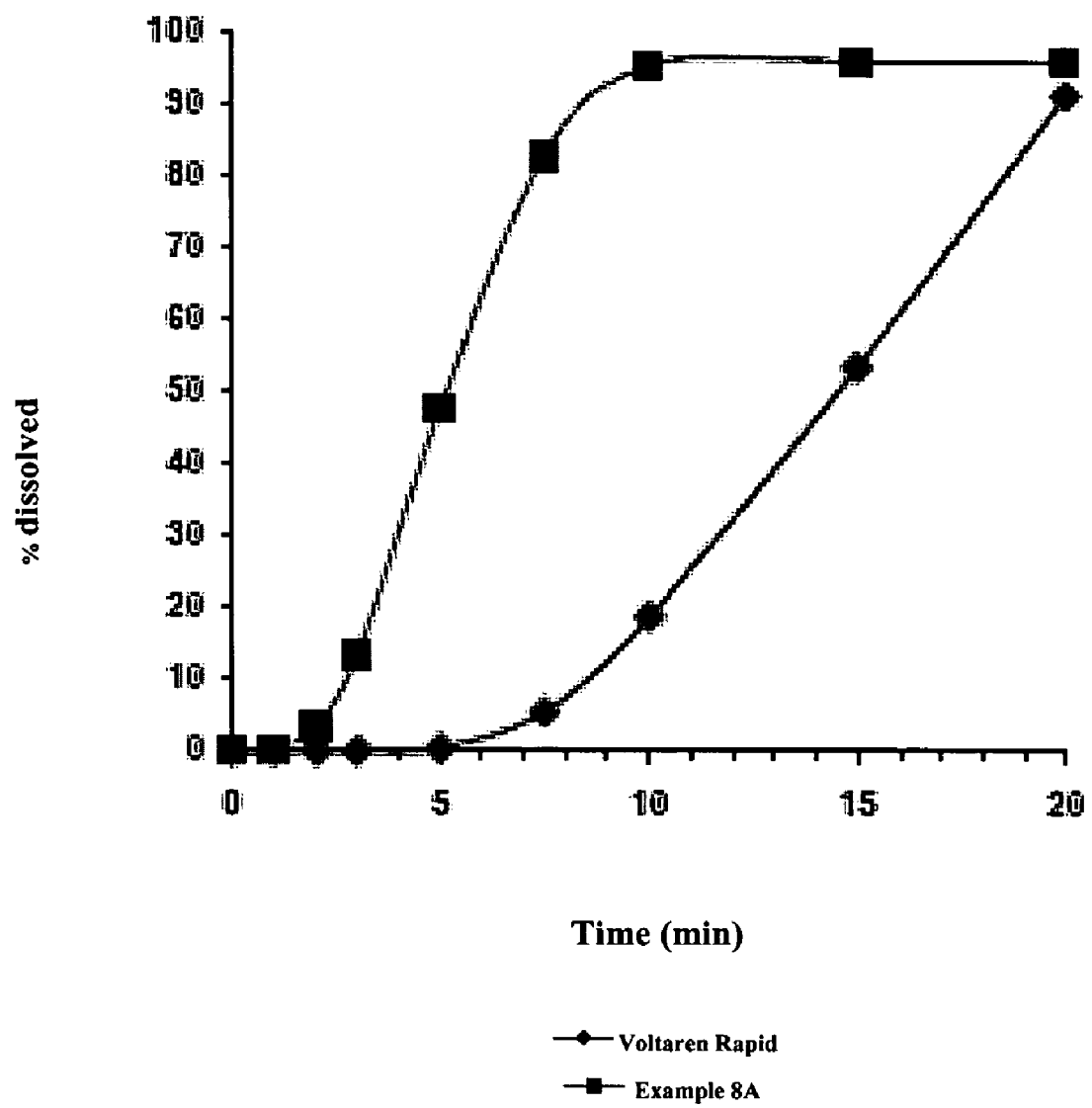
FIG. 5 is a graphical depiction of the dissolution profiles for Voltarene Rapide™ and the formulation of Example 8A.
Figure 6:
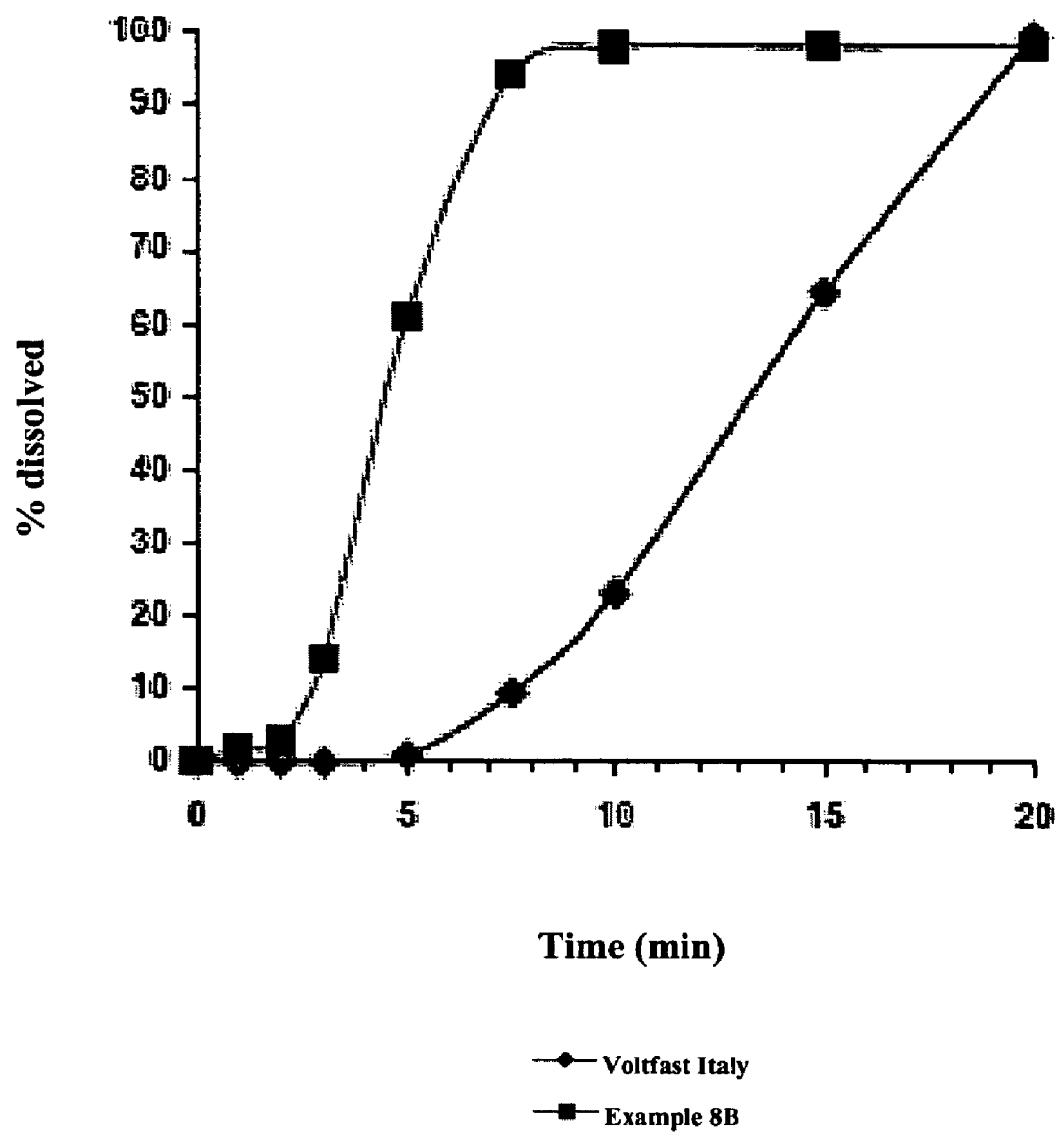
FIG. 6 is a graphical depiction of the dissolution profiles for Voltfast™ (Italy) and the formulation of Example 8B.

Using the dissolution test procedure described in the European Pharmacopeia, the dissolution profiles for two tablets (Ex. 8a and 8b) having the composition set forth in Table 8 were generated. The only difference between the two tablets was the source of the diclofenac potassium. Dissolution profiles of 50 mg. diclofenac potassium tablets marketed as Voltaren Rapid and Voltfast were also generated, and graphs of the contrasting dissolution profiles were superimposed, to produce FIGS. 5 and 6 hereto.

TABLE 16

Composition of Test Formulations

| Names of Ingredients | Unit (mg.) | Function | Reference to Standards |
|---|---|---|---|
| Drug Substance | | | |
| Diclofenac Potassium | 50.0 | Anti-inflammatory agent | Eur. Ph. |

TABLE 16-continued

Composition of Test Formulations

| Names of Ingredients | Unit (mg.) | Function | Reference to Standards |
|---|---|---|---|
| Matrix Tablet Excipients | | | |
| Potassium Bicarbonate | 22.0 | Buffering Agent | Eur. Ph. |
| Mannitol | 116.4 | Diluent and Disintegrant Agent | Eur. Ph. |
| Sodium Lauryl Sulfate | 0.1 | Solubilizing Agent | Eur. Ph. |
| Macrogols (as Macrogol 6000) | 1.5 | Lubricant Agent | Eur. Ph. |
| Crospovidone | 6.0 | Binder | Eur. Ph. |
| Magnesium Stearate | 4.0 | Lubricant Agent | Eur. Ph. |
| Film-Coating Excipients | | | |
| Clear Opadry | 4.0 | Coating Agent | In House Specifications |
| Total Weight | 204.0 | | |

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating acute pain in a host in need thereof comprising orally administering diclofenac potassium in an intact rapidly bioavailable tablet or capsule dosage form comprising (i) a $T_{max}$ of from about 5 to about 30 minutes, and (ii) a $C_{max}$ of from about 1500 to about 2500 ng/ml, and (iii) an excipient base comprising means for generating a gaseous and alkaline environment for said diclofenac potassium when orally ingested into the stomach, wherein said $T_{max}$ and $C_{max}$ are mean values obtained from a plurality of patients, and said means comprises an alkali metal carbonate or bicarbonate.

2. The method of claim 1 wherein said means and said diclofenac potassium are present in a weight ratio of from about 1:5 to about 4:5.

3. The method of claim 1 wherein said tablet or capsule comprises from about 5 to about 20 wt. % of said means.

4. The method of claim 1 wherein said means yields a pH greater than 7.2 and less than about 8.5 when said tablet or capsule is mixed with 200 ml, water at 25 degrees Celsius.

5. The method of claim 1 wherein said $T_{max}$ has been characterized as having an inter-subject variability of less than about 49%.

6. The method of claim 1 wherein said dosage form is a tablet comprising about 50 mg, of diclofenac potassium.

7. The method of claim 1 wherein said dosage form is a capsule comprising about 50 mg, of diclofenac potassium.

8. The method of claim 1 wherein said dosage form is a tablet, wherein said tablet has a disintegration time that increases as the hardness of the tablet decreases.

9. The method of claim 1 wherein said dosage form is a tablet, wherein said tablet has a disintegration time that increases as the moisture absorption by the tablet increases.

10. The method of claim 1 wherein said dosage form has been characterized as yielding one $C_{max}$ peak when orally ingested.

11. The method of claim 1 wherein said means absorbs greater than 1 wt. % moisture when maintained in a humidity chamber at 80% relative humidity and 25 degrees Celsius for 24 hours.

12. The method of claim 1 wherein said tablet or capsule comprises at least 20 wt. % of excipients that are freely soluble in water and from about 30 to about 80 wt. % of a hygroscopic diluent, wherein the weight ratio of hygroscopic diluent to freely soluble diluent is from about 1:20 to about 5:1.

13. The method of claim 1 wherein said tablet comprises a wetting agent having a hydrophilic lipophilic balance (HLB) of greater than 14.

14. The method of claim 1 wherein said tablet comprises from about 30 to about 80 wt. % of a hygroscopic diluent and a freely soluble diluent at a weight ratio of from about 1:20 to about 5:1.

15. A method of treating acute pain in a host in need thereof comprising orally administering diclofenac potassium in an intact rapidly bioavailable tablet or capsule dosage form comprising (i) a $T_{max}$ of from about 5 to about 30 minutes, and (ii) a $C_{max}$ of from about 1700 to about 2300 ng/ml, and (iii) an excipient base comprising means for generating a gaseous and alkaline environment for said diclofenac potassium when orally ingested into the stomach wherein said $T_{max}$ and $C_{max}$ are mean values obtained from a plurality of patients, and said means comprises an alkali metal carbonate or bicarbonate.

16. The method of claim 15 wherein said means and said diclofenac potassium are present in a weight ratio of from about 1:5 to about 4:5.

17. The method of claim 15 wherein said tablet or capsule comprises from about 5 to about 20 wt. % of said means.

18. The method of claim 15 wherein said means yields a pH greater than 7.2 and less than about 8.5 when said tablet or capsule is mixed with 200 ml. water at 25 degrees Celsius.

19. The method of claim 15 wherein said $T_{max}$ has been characterized as having an inter-subject variability of less than about 49%.

20. The method of claim 15 wherein said dosage form is a tablet comprising about 50 mg. of diclofenac potassium.

21. The method of claim 15 wherein said dosage form is a capsule comprising about 50 mg. of diclofenac potassium.

22. The method of claim 15 wherein said dosage form is a tablet, wherein said tablet has a disintegration time that increases as the hardness of the tablet decreases.

23. The method of claim 15 wherein said dosage form has been characterized as yielding one $C_{max}$ peak when orally ingested.

24. The method of claim 15 wherein said means absorbs greater than 1 wt. % moisture when maintained in a humidity chamber at 80% relative humidity and 25 degrees Celsius for 24 hours.

25. The method of claim 15 wherein said tablet or capsule comprises at least 20 wt. % of excipients that are freely soluble in water.

26. The method of claim 15 wherein said tablet comprises a wetting agent.

27. The method of claim 15 wherein said tablet comprises from about 30 to about 80 wt. % of a hygroscopic diluent and a freely soluble diluent at a weight ratio of from about 1:20 to about 5:1.

28. A method of treating acute pain in a host in need thereof comprising orally administering diclofenac potassium in an intact rapidly bioavailable tablet or capsule dosage form comprising (i) a $T_{max}$ of from about 5 to about 30 minutes, and (ii) a $C_{max}$ of from about 1500 to about 2500 ng/ml, and (iii) from about 7 to about 20 wt. % of a hygroscopic excipient that comprises an alkali metal carbonate or bicarbonate and that absorbs greater than 1 wt. % moisture when maintained in a humidity chamber at 80% relative humidity and 25 degrees Celsius for 24 hours, wherein said $T_{max}$ and $C_{max}$ are mean values obtained from a plurality of patients.

29. The method of claim 28 wherein said hygroscopic excipient is sodium bicarbonate or potassium bicarbonate.

30. The method of claim 28 wherein said $T_{max}$ has been characterized as having an inter-subject variability of less than about 49%.

31. The method of claim 28 wherein said dosage form is a tablet comprising about 50 mg. of diclofenac potassium, and said $C_{max}$ is from about 1700 to about 2300 ng/ml.

32. The method of claim 28 wherein said dosage form is a capsule comprising about 50 mg. of diclofenac potassium, and said $C_{max}$ is from about 1700 to about 2300 ng/ml.

33. The method of claim 28 wherein said dosage form is a tablet, wherein said tablet has a disintegration time that increases as the hardness of the tablet decreases.

34. The method of claim 28 wherein said dosage form has been characterized as yielding one $C_{max}$ peak when orally ingested.

35. A method of treating acute pain in a host in need thereof comprising orally administering diclofenac potassium in an intact rapidly bioavailable tablet or capsule dosage form comprising (i) a $T_{max}$ of from about 5 to about 30 minutes, and (ii) a $C_{max}$ of from about 1500 to about 2500 ng/ml, and (iii) an alkali metal carbonate or bicarbonate, and (iv) a hygroscopicity of greater than about 1 wt. % water absorption within a twenty four hour period in a humidity chamber maintained at 80% relative humidity, wherein said $T_{max}$ and $C_{max}$ are mean values obtained from a plurality of patients.

36. The method of claim 35 wherein said $T_{max}$ has been characterized as having an inter-subject variability of less than about 49%.

37. The method of claim 35 wherein said-dosage form is a tablet comprising about 50 mg. of diclofenac potassium, and said $C_{max}$ is from about 1700 to about 2300 ng/ml.

38. The method of claim 35 wherein said dosage form is a capsule comprising about 50 mg. of diclofenac potassium, and said $C_{max}$ is from about 1700 to about 2300 ng/ml.

39. The method of claim 35 wherein said dosage form is a tablet, wherein said tablet has a disintegration time that increases as the hardness of the tablet decreases.

40. The method of claim 35 wherein said dosage form has been characterized as yielding one $C_{max}$ peak when orally ingested.

41. A method of treating acute pain in a host in need thereof comprising orally administering diclofenac potassium in an intact rapidly bioavailable tablet or capsule dosage form comprising (i) a $T_{max}$ of from about 5 to about 30 minutes, and (ii) a $C_{max}$ of from about 1500 to about 2500 ng/ml, and (iii) an alkali metal carbonate or bicarbonate, and (iv) at least 20 wt. % of excipients that are freely soluble in water, wherein said $T_{max}$ and $C_{max}$ are mean values obtained from a plurality of patients.

42. The method of claim 41 wherein said freely soluble excipient is mannitol, lactose, sucrose, or a combination thereof.

43. The method of claim 41 wherein said $T_{max}$ has been characterized as having an inter-subject variability of less than about 49%.

44. The method of claim 41 wherein said dosage form is a tablet comprising about 50 mg. of diclofenac potassium, and said $C_{max}$ is from about 1700 to about 2300 ng/ml.

45. The method of claim 41 wherein said dosage form is a capsule comprising about 50 mg. of diclofenac potassium, and said $C_{max}$ is from about 1700 to about 2300 ng/ml.

46. The method of claim 41 wherein said dosage form is a tablet, wherein said tablet has a disintegration time that increases as the hardness of the tablet decreases.

47. The method of claim 41 wherein said dosage form has been characterized as yielding one $C_{max}$ peak when orally ingested.

48. A method of treating acute pain in a host in need thereof comprising orally administering diclofenac potassium in an intact rapidly bioavailable tablet or capsule dosage form comprising (i) a $T_{max}$ of from about 5 to about 30 minutes, and (ii) a $C_{max}$ of from about 1500 to about 2500 ng/ml, and (iii) an alkali metal carbonate or bicarbonate, and (iv) a wetting agent, wherein said $T_{max}$ and $C_{max}$ are mean values obtained from a plurality of patients.

49. The method of claim 48 wherein said wetting agent has an hydrophilic lipophilic balance (HLB) of greater than about 14.

50. The method of claim 48 wherein said wetting agent is sodium lauryl sulfate.

51. The method of claim 48 wherein said $T_{max}$ has been characterized as having an inter-subject variability of less than about 49%.

52. The method of claim 48 wherein said dosage form is a tablet comprising about 50 mg. of diclofenac potassium, and said $C_{max}$ is from about 1700 to about 2300 ng/ml.

53. The method of claim 48 wherein said dosage form is a capsule comprising about 50 mg. of diclofenac potassium, and said $C_{max}$ is from about 1700 to about 2300 ng/ml.

54. The method of claim 48 wherein said dosage form is a tablet, wherein said tablet has a disintegration time that increases as the hardness of the tablet decreases.

55. The method of claim 48 wherein said dosage form has been characterized as yielding one $C_{max}$ peak when orally ingested.

56. A method of treating acute pain in a host in need thereof comprising orally administering diclofenac potassium in an intact rapidly bioavailable tablet or capsule dosage form comprising (i) a $T_{max}$ of from about 5 to about 30 minutes, and (ii)

a $C_{max}$ of from about 1500 to about 2500 ng/ml, and (iii) from about 30 to about 80 wt. % of a hygroscopic diluent that comprises an alkali metal carbonate or bicarbonate and a freely soluble diluent at a weight ratio of from about 1:20 to about 5:1, wherein said $T_{max}$ and $C_{max}$ are mean values obtained from a plurality of patients.

57. The method of claim 56 wherein said ratio is from about 1:10 to about 3:1.

58. The method of claim 56 wherein said dosage form is a tablet, wherein said tablet has a disintegration time that increases as the hardness of the tablet decreases.

59. The method of claim 56 wherein said dosage form has been characterized as yielding one $C_{max}$ peak when orally ingested, and said $C_{max}$ is from about 1700 to about 2300 ng/ml.

* * * * *